US010082482B2

(12) United States Patent
Akimoto et al.

(10) Patent No.: US 10,082,482 B2
(45) Date of Patent: Sep. 25, 2018

(54) GAS SENSOR CONTROL APPARATUS

(71) Applicant: DENSO CORPORATION, Kariya, Aichi-pref. (JP)

(72) Inventors: Katsuhide Akimoto, Kariya (JP); Shuuichi Nakano, Kariya (JP); Yushi Fukuda, Kariya (JP); Tomofumi Fujii, Kariya (JP); Takahito Masuko, Kariya (JP); Toshihide Kumazaki, Kariya (JP)

(73) Assignee: DENSO CORPORATION, Kariya (JP)

( * ) Notice: Subject to any disclaimer, the term of this patent is extended or adjusted under 35 U.S.C. 154(b) by 388 days.

(21) Appl. No.: 14/896,100

(22) PCT Filed: Jun. 4, 2014

(86) PCT No.: PCT/JP2014/064825
§ 371 (c)(1),
(2) Date: Dec. 4, 2015

(87) PCT Pub. No.: WO2014/196559
PCT Pub. Date: Dec. 11, 2014

(65) Prior Publication Data
US 2016/0123922 A1 May 5, 2016

(30) Foreign Application Priority Data
Jun. 4, 2013 (JP) .................................. 2013-117553

(51) Int. Cl.
*G01N 27/26* (2006.01)
*G01N 27/416* (2006.01)
(Continued)

(52) U.S. Cl.
CPC ..... *G01N 27/4163* (2013.01); *F02D 41/1454* (2013.01); *F02D 41/222* (2013.01);
(Continued)

(58) Field of Classification Search
None
See application file for complete search history.

(56) References Cited

U.S. PATENT DOCUMENTS

| 5,781,878 A | 7/1998 | Mizoguchi et al. |
| 6,286,493 B1 | 9/2001 | Aoki |
| 2002/0179443 A1 | 12/2002 | Hada et al. |

(Continued)

FOREIGN PATENT DOCUMENTS

| JP | 8-338823 | 12/1996 |
| JP | 2000-258387 | 9/2000 |

(Continued)

OTHER PUBLICATIONS

International Search Report for PCT/JP2014/064825, dated Aug. 26, 2014, 4 pages.

(Continued)

*Primary Examiner* — Eli S Mekhlin
(74) *Attorney, Agent, or Firm* — Nixon & Vanderhye PC

(57) ABSTRACT

A sensor element of an A/F sensor AS has a solid electrolyte layer, a first electrode arranged on one side of the solid electrolyte layer so as to be exposed to the exhaust gas of an internal combustion engine, and a second electrode arranged on the other side of the solid electrolyte layer so as to face an atmospheric air chamber. The sensor element generates a sensor output according to the oxygen concentration in the exhaust gas. A microcomputer supplies oxygen to the first electrode side from the second electrode side via the solid electrolyte layer by applying a predetermined voltage between the pair of electrodes of the sensor element. Moreover, the microcomputer determines a crack abnormality of the solid electrolyte layer based on electric current between the pair of electrodes which is generated with start of the oxygen supply.

18 Claims, 12 Drawing Sheets

(51) Int. Cl.
*G01N 27/417* (2006.01)
*G01N 27/406* (2006.01)
*G01N 27/41* (2006.01)
*F02D 41/22* (2006.01)
*F02D 41/14* (2006.01)

(52) U.S. Cl.
CPC ......... *G01N 27/4065* (2013.01); *G01N 27/41* (2013.01); *G01N 27/4175* (2013.01); *Y02T 10/40* (2013.01)

(56) References Cited

U.S. PATENT DOCUMENTS

| | | | |
|---|---|---|---|
| 2007/0012564 A1 | 1/2007 | Hayashi et al. | |
| 2007/0045112 A1* | 3/2007 | Tashiro | F02D 41/123 204/401 |
| 2008/0262704 A1 | 10/2008 | Kawase et al. | |
| 2009/0084677 A1* | 4/2009 | Kawase | G01N 27/4065 204/402 |
| 2011/0279129 A1 | 11/2011 | Suzuki | |

FOREIGN PATENT DOCUMENTS

| | | |
|---|---|---|
| JP | 2006-113081 | 4/2006 |
| JP | 2007-024581 | 2/2007 |
| JP | 2007-064873 | 3/2007 |
| JP | 2007-132717 | 5/2007 |
| JP | 2007-232709 | 9/2007 |
| JP | 2008-082295 | 4/2008 |
| JP | 2008-267230 | 11/2008 |
| JP | 2009-085637 | 4/2009 |
| JP | 2009-250690 | 10/2009 |
| JP | 2011-242147 | 12/2011 |

OTHER PUBLICATIONS

International Preliminary Report on Patentability for PCT/JP2014/064825 dated Dec. 8, 2015 (17 pgs.).

* cited by examiner (a) IN NORMAL STATE (b) IN Zr-CRACKED STATE

FIG.11
(a)
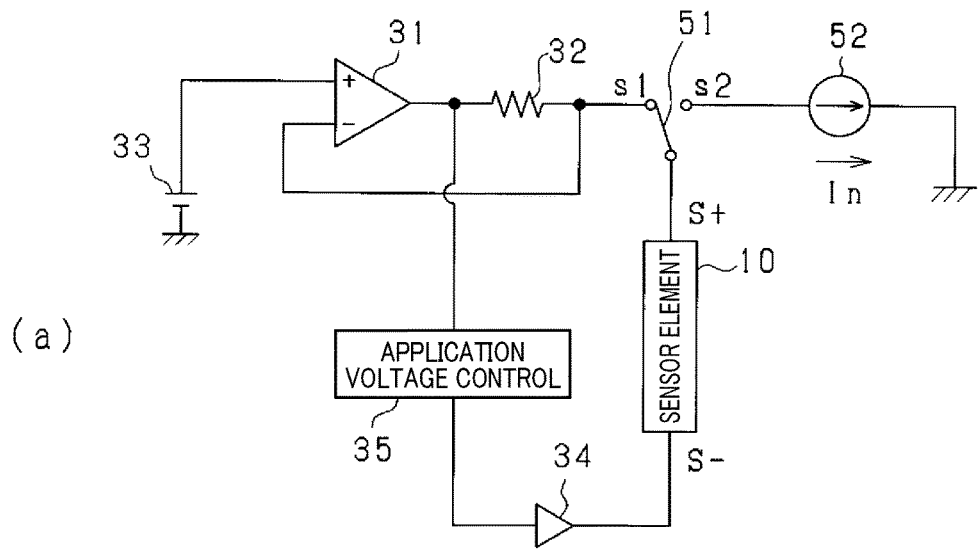
(b)
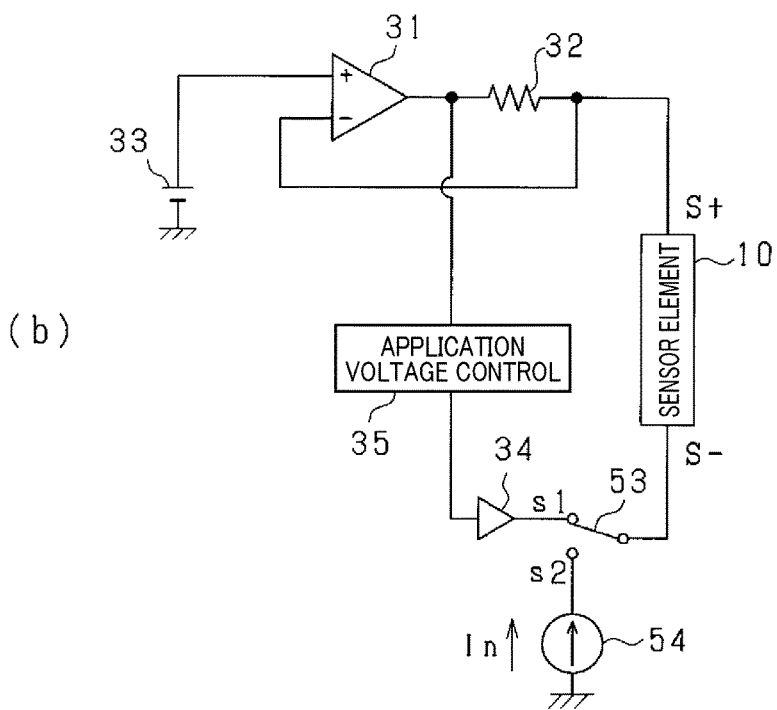

(a) IN NORMAL STATE — ELECTROMOTIVE FORCE SMALL (b) IN Zr-CRACKED STATE — ELECTROMOTIVE FORCE LARGE

GAS SENSOR CONTROL APPARATUS

This application is the U.S. national phase of International Application No. PCT/JP2014/064825 filed 4 Jun. 2014, which designated the U.S. and claims priority to JP Patent Application No. 2013-117553 filed 4 Jun. 2013, the entire contents of each of which are hereby incorporated by reference.

TECHNICAL FIELD

The present invention relates to a control apparatus of a gas sensor that generates a sensor output according to the oxygen concentration in an exhaust gas.

BACKGROUND ART

Conventionally, gas sensors that employ a solid electrolyte such as stabilized zirconia have been used as, for example, a sensor for sensing the concentration of oxygen contained in the exhaust gas from an on-vehicle engine. Moreover, various techniques have been proposed for eliminating sensing errors of these gas sensors.

For example, there has been known a technique of acquiring a sensor output value under a condition where a fuel cut is performed in an engine and calculating, as an output correction value, a deviation of the sensor output value based on a comparison between the sensor output value and a known reference output value in an atmospheric air condition (see, for example, Patent Document 1). In this case, a correction gain is calculated using the output correction value (atmospheric air output error) calculated in an atmospheric air correction process, and a correction of the sensor output value is performed using the correction gain when the air/fuel ratio is deviated from the stoichiometric ratio (theoretical air/fuel ratio).

PRIOR ART LITERATURE

Patent Literature

[Patent Document 1] Japanese Patent Application Publication No. JP2008267230A

SUMMARY OF THE INVENTION

Problems to be Solved by the Invention

As described above, it is possible to perform a gain correction of the sensor output value by using the correction gain calculated by the atmospheric air correction process. For example, when the gas sensor is configured as an A/F (Air/Fuel ratio) sensor to include a diffusion layer, it is possible to correct a gain error which occurs upon occurrence of clogging and/or cracks of the diffusion layer.

However, besides clogging and/or cracks of the diffusion layer, cracks of a solid electrolyte layer may occur as an abnormality of the gas sensor. Upon occurrence of cracks in the solid electrolyte layer, the exhaust gas flows into an atmospheric air chamber through the cracks, causing output errors to occur. In this case, a deviation (error) of the sensor output value occurs even at the stoichiometric ratio. In the existing art, a determination of such a crack abnormality of the solid electrolyte layer is not performed; thus it is impossible to identify the abnormality type with respect to the crack abnormality of the solid electrolyte layer.

Furthermore, if cracks of the solid electrolyte layer are not identified though they have occurred and the gain correction based on the atmospheric air correction process is performed, there is a concern that an erroneous correction may be performed on the sensor output value.

The present invention mainly aims to provide a gas sensor control apparatus which can properly determine a crack abnormality of a solid electrolyte layer upon occurrence of it in a gas sensor.

Means for Solving the Problems

Hereinafter, means for solving the above problems and advantageous effects thereof will be described.

A gas sensor control apparatus according to the present invention is provided for controlling a gas sensor. The gas sensor includes a sensor element that has a solid electrolyte layer, a first electrode arranged on one side of the solid electrolyte layer so as to be exposed to the exhaust gas of an internal combustion engine, and a second electrode arranged on the other side of the solid electrolyte layer so as to face an atmospheric air chamber. The gas sensor generates a sensor output according to the oxygen concentration in the exhaust gas. The gas sensor control apparatus is characterized by including: an oxygen supply means for supplying oxygen to the first electrode side from the second electrode side via the solid electrolyte layer by applying a predetermined voltage or a predetermined electric current between the first and second electrodes; and an abnormality determination means for determining a crack abnormality of the solid electrolyte layer based on electric current or electromotive force between the first and second electrodes which is generated with start of the oxygen supply by the oxygen supply means.

In the sensor element of the gas sensor, when cracks have occurred in the solid electrolyte layer, the exhaust gas flows into the atmospheric air chamber through the cracks, lowering the oxygen concentration in the atmospheric air chamber. In this case, compared to a normal state, the oxygen concentration in the atmospheric air chamber becomes lower. Therefore, when the predetermined voltage is applied to the first and second electrodes, the oxygen supply quantity (oxygen pumping quantity) caused by the voltage application is less, and it is more difficult for electric current to flow between the first and second electrodes. Moreover, when the predetermined electric current is applied to the first and second electrodes, the oxygen supply quantity (oxygen pumping quantity) caused by the electric current application is less, and the sensor electromotive force generated by the oxygen supply is larger. Since there are generated the above differences between a crack abnormality state where cracks have occurred in the solid electrolyte layer and the normal state where no cracks have occurred in the solid electrolyte layer, it is possible to properly determine the crack abnormality of the solid electrolyte layer using the above differences.

BRIEF DESCRIPTION OF THE DRAWINGS

FIG. 11 is a schematic view illustrating the configuration of a sensor control circuit according to a second embodiment.

EMBODIMENTS FOR CARRYING OUT THE INVENTION

First Embodiment

In the present embodiment, an air/fuel ratio detecting apparatus is embodied which detects, taking the exhaust gas discharged from an on-vehicle engine (internal combustion engine) as a detected gas, the oxygen concentration (air/fuel ratio: A/F ratio) in the exhaust gas. The detection results of the air/fuel ratio are used in an air/fuel ratio control system that is configured with an engine ECU and so on. In the air/fuel ratio control system, controls are properly performed which include, for example, a stoichiometric air/fuel ratio control for feedback-controlling the air/fuel ratio in the vicinity of the stoichiometric ratio and a lean air/fuel ratio control for feedback-controlling the air/fuel ratio in a predetermined lean region.

Figure 2:
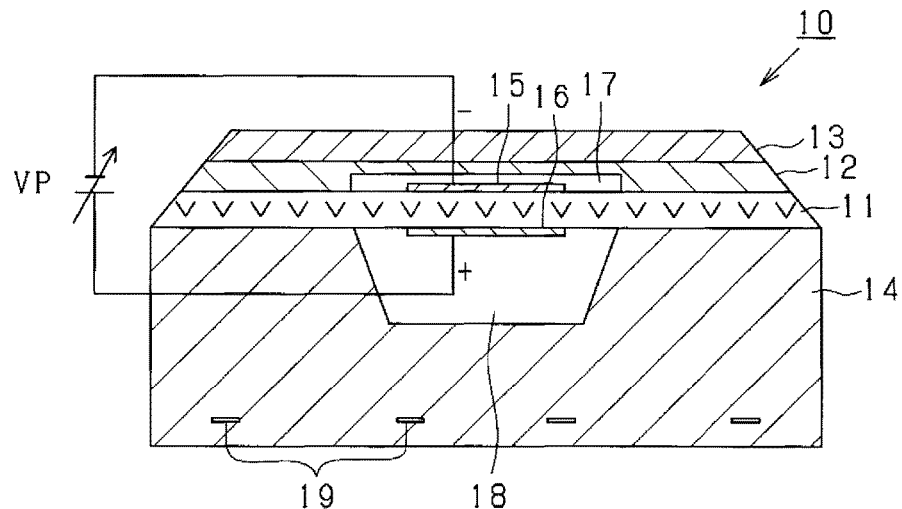
FIG. 2 is a cross-sectional view illustrating the configuration of a sensor element.

First, an element structure of the A/F sensor (Air/Fuel ratio sensor) according to the present embodiment will be described with reference to FIG. 2. The A/F sensor is provided in an exhaust pipe of the engine to generate, taking the exhaust gas flowing in the exhaust pipe as a detection target, a sensor output according to the oxygen concentration in the exhaust gas. The A/F sensor includes a sensor element 10 which includes a solid electrolyte body and in which an element current flows according to the oxygen concentration in the exhaust gas in a voltage-applied state. FIG. 2 shows the cross-sectional configuration of the sensor element 10 that is constituted of a laminated structure. The sensor element 10 actually has a long shape extending in a direction perpendicular to the paper surface of FIG. 2. The sensor element 10 is configured so as to be entirely received in a housing or an element cover.

The sensor element 10 includes a solid electrolyte layer 11, a diffusion resistance layer 12, a shield layer 13 and an insulation layer 14, which are laminated in the vertical direction of the figure. Around the element, there is provided a not-shown protective layer. The rectangular plate-shaped solid electrolyte layer 11 is a sheet made of partially-stabilized zirconia. A pair of electrodes 15 and 16 are vertically opposed to each other with the solid electrolyte layer 11 interposed therebetween. Of the pair of electrodes 15 and 16, the electrode 15 is a first electrode (exhaust gas-side electrode) while the electrode 16 is a second electrode (atmospheric air-side electrode). The diffusion resistance layer 12 is formed of a porous sheet for introducing the exhaust gas to the electrode 15. The shield layer 13 is formed of a dense layer for suppressing permeation of the exhaust gas. In the diffusion resistance layer 12, there is provided an exhaust gas chamber 17 so as to surround the electrode 15. The diffusion resistance layer 12 and the shield layer 13 are each obtained by shaping ceramic, such as alumina, spinel or zirconia, using a sheet shaping method, but have different gas-permeabilities due to differences in average pore diameter and porosity.

The insulation layer 14 is formed of a highly heat-conductive ceramic such as alumina. In a portion of the insulation layer 14 facing the electrode 16, there is formed an atmospheric air duct 18 as an atmospheric air chamber. Moreover, in the insulation layer 14, there is embedded a heater 19. The heater 19 is constituted of a linear heat-generating body that generates heat upon supply of electric current from a battery power source, thereby heating the entire element.

In the sensor element 10 of the above configuration, the surrounding exhaust gas is introduced from a side portion of the diffusion resistance layer 12, and then flows into the exhaust gas chamber 17 via the diffusion resistance layer 12, reaching the electrode 15. When the exhaust gas is lean, oxygen in the exhaust gas is decomposed at the electrode 15, and then discharged to the atmospheric air duct 18 by the electrode 16. In contrast, when the exhaust gas is rich, oxygen in the atmospheric air duct 18 is decomposed at the electrode 16, and then discharged to the exhaust gas side by the electrode 15.

In the present embodiment, the exhaust gas-side electrode 15 is defined as a negative electrode, and the atmospheric air-side electrode 16 is defined as a positive electrode. As shown in FIG. 2, with the electrode 15 being negative (−) and the electrode 16 being positive (+), the application voltage VP applied between the electrodes is defined as a positive voltage. Therefore, in contrast, with the electrode 15 being positive (+) and the electrode 16 being negative (−), the application voltage VP applied between the electrodes is a negative voltage.

Figure 3:
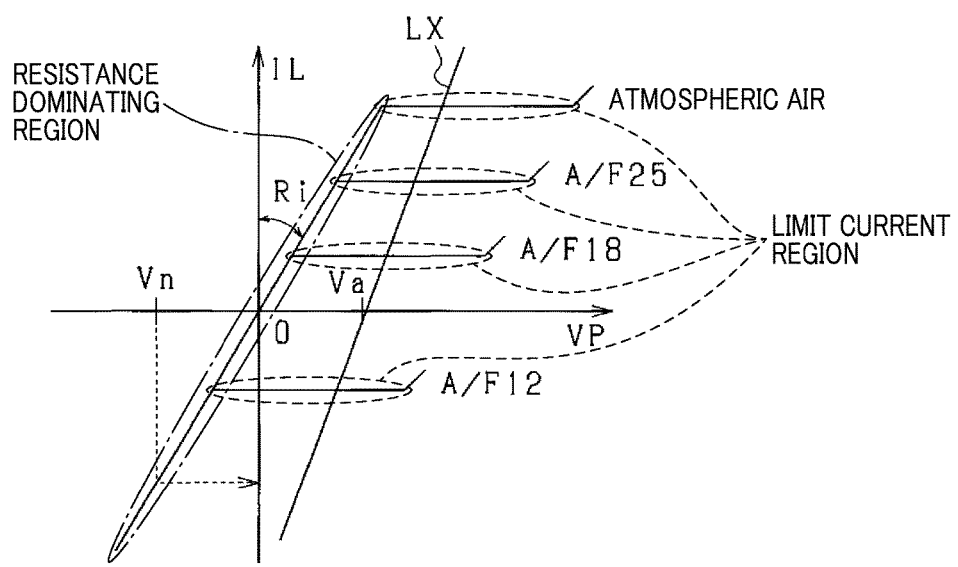
FIG. 3 is a schematic view illustrating the output characteristics of an A/F sensor.

FIG. 3 illustrates the output characteristics (V-I characteristics) of the sensor element 10. In FIG. 3, the horizontal axis indicates the application voltage VP of the sensor element 10, and the vertical axis indicates the element current IL. Moreover, of the characteristic lines of FIG. 3, those straight-line portions (flat portions) which are parallel to the horizontal axis VP define a limit current region for identifying the element current IL as the limit current. The increase and decrease of the element current IL corresponds to the increase and decrease of the air/fuel ratio (or the degree of being lean or rich). That is, the element current IL increases as the air/fuel ratio is shifted to the lean side, and decreases as the air/fuel ratio is shifted to the rich side. In FIG. 3, LX designates an application voltage characteristic line for determining the application voltage VP, whose slope is approximately identical to that of a resistance dominating region (an inclined portion on the lower voltage side of the limit current region). For example, when the air/fuel ratio is equal to the stoichiometric ratio, Va is applied between the two electrodes of the sensor element 10.

Next, the configuration of a gas sensor control apparatus according to the present embodiment will be described with reference to FIG. 1.

Figure 1:
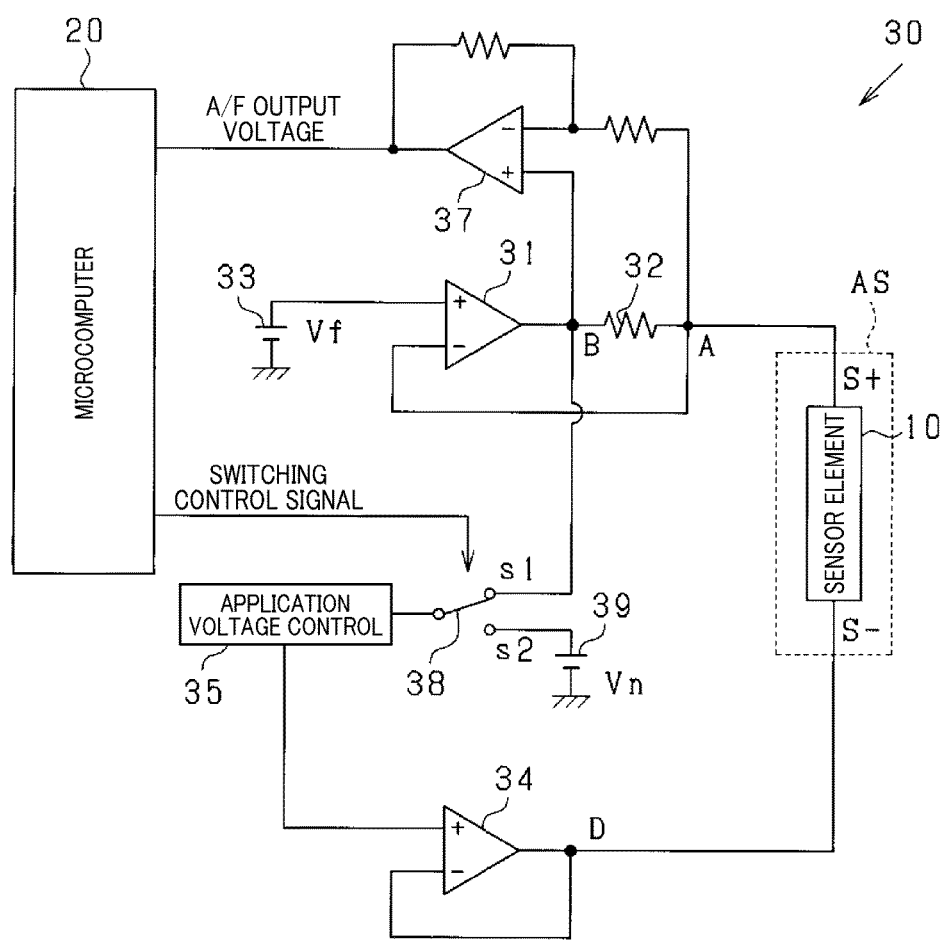
FIG. 1 is a schematic view illustrating the overall configuration of a gas sensor control apparatus according to a first embodiment.

As shown in FIG. 1, the gas sensor control apparatus according to the present embodiment mainly includes a microcomputer 20 and a sensor control circuit 30, by which measurement of the element current flowing in the sensor element 10 of the A/F sensor AS and calculation of the A/F value based on the element current value are performed. The microcomputer 20 is constituted of a well-known logic-arithmetic circuit which includes a CPU, various memories and an A/D converter. The microcomputer 20 receives an A/F output voltage, which corresponds to the element current from the sensor control circuit 30, and calculates the A/F value based on the A/D value of the A/F output voltage. The A/F value calculated by the microcomputer 20 is successively outputted to a not-shown engine ECU.

Moreover, in the sensor control circuit 30, to a positive terminal (S+ terminal connected to the atmospheric air-side electrode 16) of the sensor element 10, there is connected a reference voltage power source 33 via an operational amplifier 31 and a current detection resistor (resistor for measuring current) 32; to a negative terminal (S− terminal connected to the exhaust gas-side electrode 15) of the sensor element 10, there is connected an application voltage control circuit 35 via an operational amplifier 34. In this case, an A point at one end of the current detection resistor 32 is kept at the same voltage as the reference voltage Vf (e.g., 2.2V). The element current flows via the current detection resistor 32, and the voltage at a B point changes according to the element current. For example, when the exhaust gas is lean, the B-point voltage rises since current flows from the S+ terminal to the S− terminal in the sensor element 10; when the exhaust gas is rich, the B-point voltage drops since current flows from the S− terminal to the S+ terminal.

As a basic configuration, the application voltage control circuit 35 monitors the B-point voltage, determines the voltage to be applied to the sensor element 10 according to the value of the B-point voltage (e.g., determines based on the application voltage straight line LX of FIG. 3), and controls a D-point voltage via an operational amplifier 34. In addition, in the case of performing the A/F detection only in the vicinity of the stoichiometric ratio, it is also possible to fix the application voltage.

Moreover, to A point and B point at both ends of the current detection resistor 32, there is connected an amplifier circuit 37. The output of the amplifier circuit 37, namely the A/F output voltage, is inputted to an A/D input terminal of the microcomputer 20. The microcomputer 20 calculates the A/F value based on the A/D value of the successively-inputted A/F output voltage.

In the sensor element 10, upon occurrence of cracks in the solid electrolyte layer 11 (occurrence of Zr cracks) due to age deterioration and/or shocks, the exhaust gas flows into the atmospheric air duct 18 from the exhaust gas chamber 17 through the cracks. This may cause the oxygen concentration in the atmospheric air duct 18 to be lowered. Specifically, since the atmospheric air is introduced into the atmospheric air duct 18, the oxygen concentration therein is originally about 20.9%. However, with the exhaust gas flowing thereinto, the oxygen concentration becomes lower than 20.9%. Further, upon occurrence of the deviation of the oxygen concentration in the atmospheric air duct 18, detection errors occur in the A/F sensor AS.

Therefore, in the present embodiment, a predetermined voltage is applied to the pair of electrodes 15 and 16 of the sensor element 10 so that oxygen supply (oxygen pumping) is performed from the electrode 16 side (the reference electrode side) to the electrode 15 side (the gas detection electrode side). Then, based on the element current detected in the voltage application state, a Zr-cracked (i.e., the solid electrolyte layer 11-cracked) abnormality of the sensor element 10 is determined. In this case, the voltage applied so as to supply oxygen from the electrode 16 side to the electrode 15 side is a negative voltage, for example Vn in FIG. 3.

As a configuration of shifting the application voltage to the sensor element 10 to a negative voltage, the following configuration is added to the sensor control circuit 30 of FIG. 1. That is, in the sensor control circuit 30, there is provided a switch circuit 38 between the element current measurement point (the B point in the figure) and the application voltage control circuit 35; the switch circuit 38 is switch-operated according to a control command (switching control signal) from the microcomputer 20. In such a case, the switch circuit 38 is normally connected at an s1 point; in this state, a normal control of the A/F sensor AS is performed. That is, the B-point voltage is inputted to the application voltage control circuit 35, and the application voltage is variably regulated based on the B-point voltage. In contrast, when the switch circuit 38 is connected at an s2 point, a constant negative voltage Vn is inputted from a negative voltage power source 39 to the application voltage control circuit 35. Thus, regardless of the B-point voltage (the element current at each time), the application voltage is set by the negative voltage power source 39. In other words, when the switch circuit 38 is switched to the s1 point side, the normal application voltage control is performed; when the switch circuit 38 is switched to the s2 point side, the negative voltage control is performed.

Figure 4:
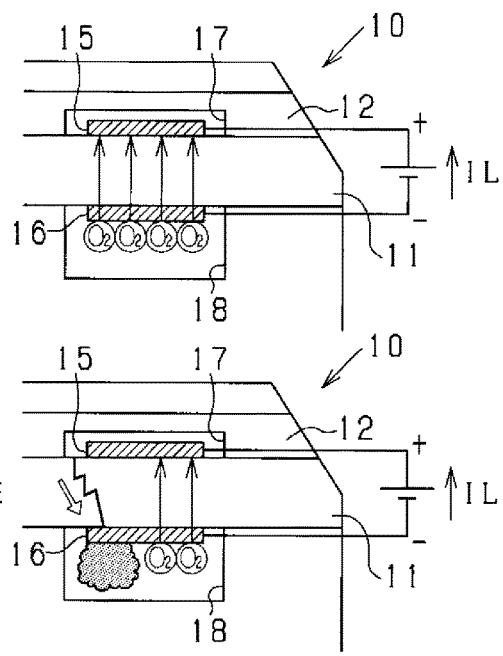
FIG. 4 is a schematic view illustrating a normal state and a Zr-cracked state of the sensor element.
Figure 5:
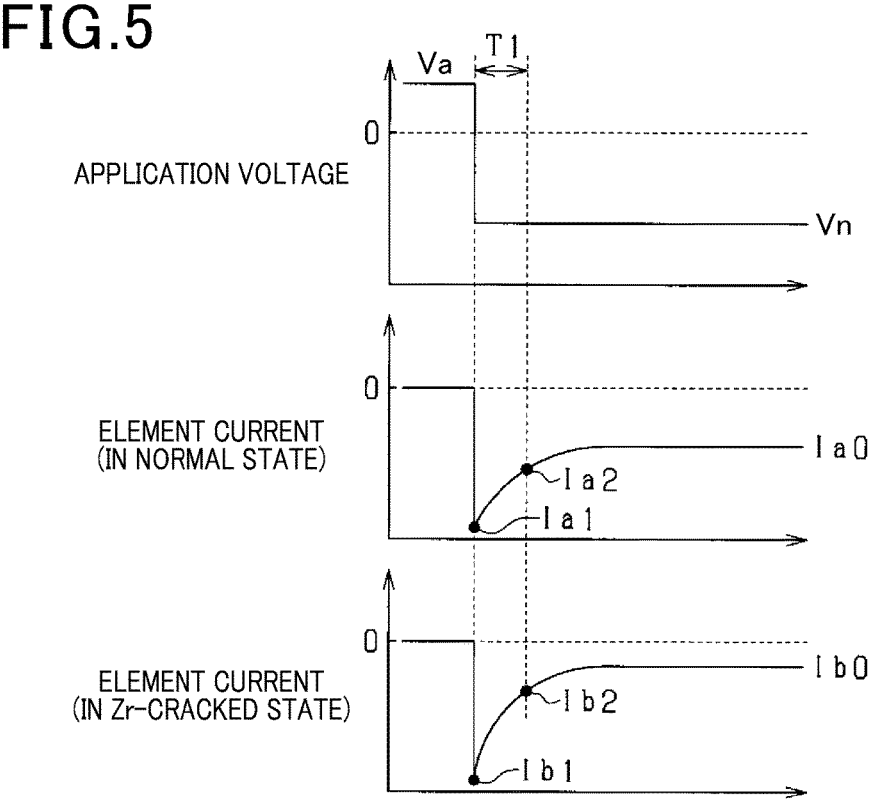
FIG. 5 is a time chart illustrating the changes with time of an application voltage and an element current in the normal state and in the Zr-cracked state.

The principle of detection of a crack abnormality by the negative voltage application will be described in detail. FIG. 4 illustrates the sensor element 10 in a normal state and in a Zr-cracked state. FIG. 5 illustrates the changes with time of the application voltage and the element current in the normal state and in the Zr-cracked state. In addition, here, the case is illustrated where the sensor application voltage is changed from a positive voltage (e.g., Va of FIG. 3) to a negative voltage (e.g., Vn of FIG. 3) in a stoichiometric ratio detection state.

First, the normal state will be described. In the normal state, the inside of the atmospheric air duct 18 is kept at the same oxygen concentration (20.9%) as the atmosphere. Moreover, in this state, when the application voltage VP is changed from the positive voltage, which is the normal application voltage, to the negative voltage, oxygen is pumped from the atmospheric air duct 18 side to the exhaust gas chamber 17 side. Consequently, the element current IL is instantly changed to a negative current, and then the negative current is gradually lowered (the negative-side current becomes small). Thereafter, the element current IL is converged to a current value Ia0 that corresponds to the Vn application state on the sensor characteristics.

In this case, the peak value of the negative current immediately after shifting the application voltage to the negative voltage is Ia1; the negative current at a time point after the elapse of a time T1 from the voltage shifting is Ia2. That is, for the period T1 of transient change of the element current, the negative current is changed from Ia1 to Ia2.

Next, the Zr-cracked state will be described. In the Zr-cracked state, the exhaust gas chamber 17 and the atmospheric air duct 18 communicate with each other via the cracks of the solid electrolyte layer 11. With the exhaust gas flowing into the atmospheric air duct 18, the oxygen concentration in the atmospheric air duct 18 becomes lower than that in the atmosphere (lower than 20.9%). Moreover, in this state, when the application voltage VP is changed from the positive voltage to the negative voltage, oxygen is pumped from the atmospheric air duct 18 side to the exhaust gas chamber 17 side. Consequently, the element current IL is instantly changed to a negative current, and then the negative current is gradually lowered (the negative-side current becomes small). Thereafter, the element current IL is converged to a current value Ib0 that corresponds to the Vn application state on the sensor characteristics.

In this case, the peak value of the negative current immediately after shifting the application voltage to the negative voltage is Ib1; the negative current at a time point after the elapse of a time T1 from the voltage shifting is Ib2. That is, for the period T1 of transient change of the element current, the negative current is changed from Ib1 to Ib2.

Comparing the normal state and the Zr-cracked state, the negative current peak values immediately after the shifting to the negative voltage are approximately equal. However, the negative current changes after that are different. The current change in the Zr-cracked state is more rapid than the current change in the normal state. Therefore, |Ia2|>|Ib2|, and (Ia2−Ia1)<(Ib2−Ib1). Moreover, |Ia0|>|Ib0|.

In short, in the Zr-cracked state, the exhaust gas flows into the atmospheric air duct 18 and thus the oxygen concentration in the atmospheric air duct 18 becomes low. Therefore, when oxygen pumping is performed from the atmospheric air duct 18 side to the exhaust gas chamber 17 side, the oxygen in the atmospheric air duct 18 is quickly reduced and thus it becomes difficult for the negative current to flow. That is, in the Zr-cracked state, it becomes more difficult for the negative current to flow when the negative voltage is applied, in comparison with the normal state. Therefore, the return (convergence) from the current peak value after shifting the application voltage is quick. In the present embodiment, based on the difference in convergence speed of the negative current, occurrence of the Zr-cracked abnormality in the sensor element 10 is determined.

Next, abnormality determination processes performed by the microcomputer 20 will be described. In the present embodiment, two abnormality determination processes are performed. In one abnormality determination process, an atmospheric air sensing value of the A/F sensor AS is calculated during a fuel cut of the engine; then based on the atmospheric air sensing value, a clogging abnormality of the diffusion resistance layer 12 and a crack abnormality of the diffusion resistance layer 12 are determined. In the other abnormality determination process, a crack abnormality of the solid electrolyte layer 11 is determined during a stoichiometric-ratio operation of the engine.

Figure 6:
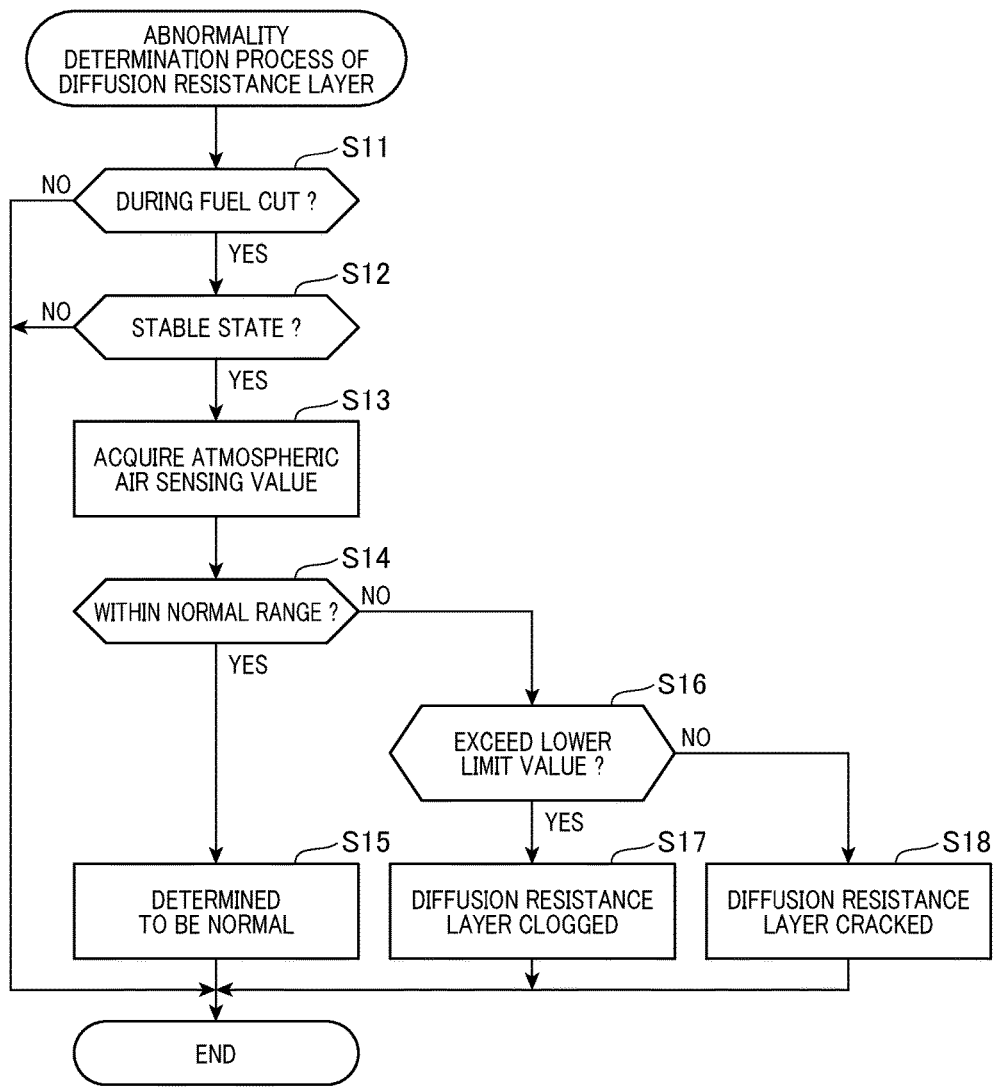
FIG. 6 is a flow chart illustrating the steps of a diffusion resistance layer abnormality determination process according to the first embodiment.

First, the abnormality determination process of the diffusion resistance layer 12 will be described. FIG. 6 is a flow chart illustrating the steps of the abnormality determination process of the diffusion resistance layer 12. This process is repeatedly performed by the microcomputer 20 in a predetermined cycle.

In FIG. 6, at step S11, it is determined whether or not it is now during a fuel cut. At subsequent step S12, it is further determined whether or not the state in the engine exhaust pipe after the start of the fuel cut is stable. Then, if both steps S11 and S12 are YES, the process proceeds to subsequent step S13, at which the current sensor output value is acquired as the atmospheric air sensing value.

Thereafter, at step S14, it is determined whether not the atmospheric air sensing value acquired at step S13 is within a normal range. Here, since the oxygen concentration in the atmosphere is known, the normal range is specified based on the known oxygen concentration. If the atmospheric air sensing value is within the normal range, step S14 is determined in the affirmative. Then, at step S15, the A/F sensor AS is determined to be normal.

Moreover, if the atmospheric air sensing value is out of the normal range, step S14 is determined in the negative. Then, at step S16, it is determined whether nor not the atmospheric air sensing value is deviated, of an upper limit value side and a lower limit value side of the normal range, to the lower limit value side. If the atmospheric air sensing value is deviated to the lower limit value side of the normal range, the process proceeds to step S17, at which it is determined that the clogging abnormality of the diffusion resistance layer 12 has occurred in the sensor element 10. In contrast, if step S16 is NO, in other words, if the atmospheric air sensing value is deviated to the upper limit value side of the normal range, the process proceeds to step S18, at which it is determined that the crack abnormality of the diffusion resistance layer 12 has occurred in the sensor element 10.

In addition, in the process of FIG. 6, it is possible to calculate the difference between the atmospheric air sensing value by the A/F sensor AS and a preset atmospheric air reference value and store the difference as an atmospheric air correction value in a memory. In this case, based on the atmospheric air correction value, a gain correction is performed on the output value of the A/F sensor AS.

Figure 7:
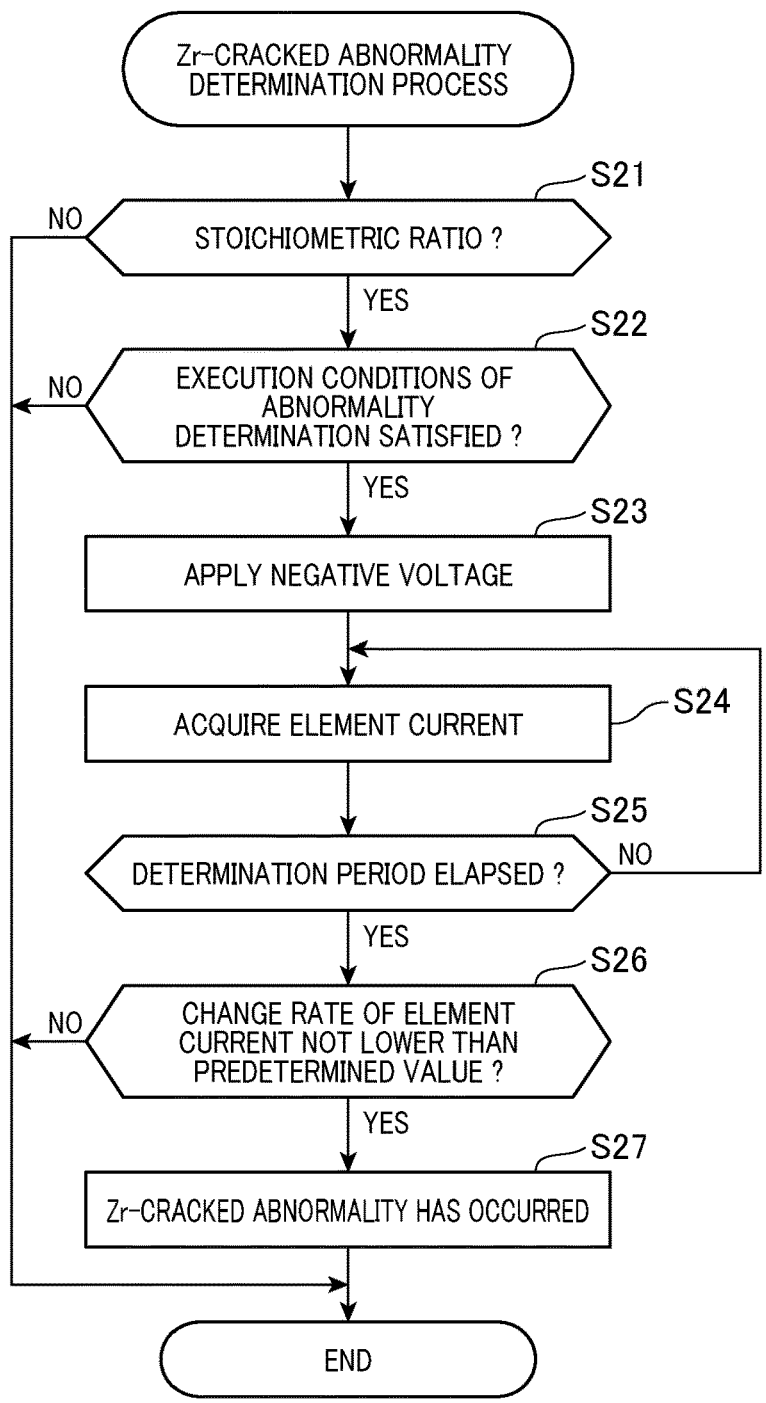
FIG. 7 is a flow chart illustrating the steps of a Zr-cracked abnormality determination process according to the first embodiment.

Next, the determination process of the crack abnormality of the solid electrolyte layer 11 (Zr-cracked abnormality) will be described. FIG. 7 is a flow chart illustrating the steps of the Zr-cracked abnormality determination process. This process is repeatedly performed by the microcomputer 20 in a predetermined cycle.

In FIG. 7, at step S21, it is determined whether or not the engine is currently in the stoichiometric-ratio operating state. If the air/fuel ratio is kept stable at the stoichiometric ratio, step S21 is determined in the affirmative. Moreover, at step S22, it is determined whether or not the following execution conditions of the abnormality determination are satisfied. Specifically, the execution conditions include:

(1) the state of the exhaust gas (the exhaust gas flow rate, the exhaust gas pressure) in the exhaust pipe is stable;
(2) the temperature of the sensor element 10 is in a constant state;
(3) it is not during or immediately after a fuel cut;
(4) the exhaust gas temperature is within a predetermined range; and
(5) the atmospheric pressure is within a predetermined range.

If all of these conditions are satisfied, step S22 is determined in the affirmative. In addition, the setting of the execution conditions of the abnormality determination is optional provided that the execution conditions include at least one of the above conditions (1)-(5).

Each of the above conditions (1)-(5) will be briefly described. First, the condition (1) is set for satisfying that the oxygen quantity in the atmospheric air duct 18 is stable. That is, when the exhaust gas flow rate or the exhaust gas pressure varies, the oxygen quantity in the atmospheric air duct 18 also varies to influence the oxygen pumping quantity from the atmospheric air duct 18 to the exhaust gas chamber 17. In this regard, if the exhaust gas flow rate and the exhaust gas pressure are in a stable state, the oxygen pumping quantity can be kept at a desired quantity. In addition, the exhaust gas flow rate may be determined to be stable from the fact that the rotational speed of the engine is kept stable at a constant value.

The condition (2) is set, focusing on the fact that the oxygen pumping quantity depends on the activation state of the sensor element 10, for keeping the oxygen pumping quantity at a desired quantity by keeping the element temperature constant at the activation temperature. For example, if the element temperature is lower than a predetermined element activation temperature, the oxygen pumping quantity is considered to be reduced due to this influence. In contrast, if the element temperature is higher than the predetermined element activation temperature, the oxygen pumping quantity is considered to be increased due to this influence. In addition, the element temperature may be determined by, for example, using a well-known impedance detection method. Specifically, the sensor application voltage or application current is temporarily changed at a predetermined AC frequency, and the element current or the element electromotive force which changes in response to the aforementioned temporary change is detected. Then, the element impedance is calculated based on the element current or the element electromotive force.

The condition (3) is set, focusing on the fact that it is difficult to detect the Zr-cracked abnormality when the difference in oxygen concentration between the gas in the exhaust gas chamber 17 and the gas in the atmospheric air duct 18 is small, for improving the determination accuracy of the Zr-cracked abnormality by securing a predetermined difference in oxygen concentration.

The condition (4) is set, focusing on the fact that the exhaust gas temperature influences the temperature of the sensor element 10 when the exhaust gas temperature is excessively high or low, for keeping the oxygen pumping quantity at a desired quantity by keeping the element temperature constant. This condition focuses on the same reduction as the above condition (2). In addition, the exhaust gas temperature may be detected by using an exhaust gas sensor provided in the engine exhaust pipe or be estimated based on the engine operating condition such as the rotational speed of the engine and the engine load.

The condition (5) is set, focusing on the fact that a change in the atmospheric pressure influences the oxygen concentration in the atmosphere, for keeping the oxygen concentration in the atmosphere constant. For example, if the atmospheric pressure becomes low, the oxygen pumping quantity is considered to be reduced due to decrease in the oxygen concentration. In contrast, if the atmospheric pressure becomes high, the oxygen pumping quantity is considered to be increased due to increase in the oxygen concentration.

If steps S21 and S22 are both YES, the process proceeds to step S23. On the other hand, if either of steps S21 and S22 is NO, the process directly goes to the end. In addition, it is also possible to set execution intervals of the abnormality determination and determine whether or not execution conditions of the abnormality determination are satisfied with one of the conditions being that a predetermined time (e.g., 10 minutes) has elapsed from the previous execution.

At step S23, the negative voltage is applied to the pair of electrodes 15 and 16 of the sensor element 10. At subsequent step S24, the value of the element current flowing in the state of application of the negative voltage is acquired. The acquisition of the element current value is repeatedly performed in a predetermined time cycle until the elapse of a predetermined abnormality determination period (i.e., until step S25 is determined in the affirmative). In terms of avoiding blackening in the solid electrolyte layer 11, it is preferable for the value of the negative voltage to be higher than or equal to −0.8V. Moreover, it is preferable for the application time of the negative voltage to be shorter than or equal to 500 msec.

If the predetermined abnormality determination period has elapsed and thus step S25 is determined in the affirmative, the process proceeds to step S26. At step S26, it is determined whether or not the Zr-cracked abnormality has occurred based on the change rate (corresponding to rate parameter) of the element current after the start of the oxygen pumping upon the shifting of the sensor application voltage to the negative voltage. Specifically, it is determined whether or not the change rate of the element current is higher than or equal to a predetermined determination threshold value K1. The change rate of the element current is a parameter representing how fast the element current changes with the elapse of time. For example, the change rate is a time differential value (slope of change) of the element current acquired at every predetermined time. Alternatively, the change rate may be the amount of the current change in a predetermined time after the start of the oxygen pumping. In FIG. 5, the amount of the current change is (Ia2−Ia1) or (Ib2−Ib1).

In addition, it is also possible to set a current threshold value for the negative current and define the change rate (rate parameter) of the element current as the time required for the element current to reach the current threshold value during the process where the negative current converges to a convergence value after the start of the oxygen pumping. In this case, the higher the change rate of the element current, the shorter the time required for the element current to reach the current threshold value.

The determination threshold value K1 is set with reference to the change rate of the element current in the normal state. If the sensor element 10 is normal, step S26 is determined in the negative. In contrast, if the Zr-cracked abnormality has occurred, step S26 is determined in the affirmative.

Moreover, if step S26 is YES, the process proceeds to step S27, at which it is determined that the Zr-cracked abnormality has occurred in the sensor element 10. In this case, with the abnormality determination processes of FIGS. 6 and 7, it is possible to identify which one of the clogging abnormality of the diffusion resistance layer 12, the crack abnormality of the diffusion resistance layer 12 and the crack abnormality of the solid electrolyte layer 11 (Zr-cracked abnormality) has occurred in the A/F sensor AS.

In addition, in the process of FIG. 7, when it is determined that the Zr-cracked abnormality has occurred, a stoichiometric ratio correction value may be calculated based on the amount of deviation of the element current (negative current) from the normal state and a correction of the sensor output value may be performed using the stoichiometric ratio correction value.

According to the present embodiment described above, the following advantageous effects are achieved.

A configuration is provided in which: the negative voltage is applied between the pair of electrode 15 and 16 to perform the oxygen pumping via the solid electrolyte layer 11; and the crack abnormality of the solid electrolyte layer 11 is determined based on the negative current generated during that time. In this case, there is generated the difference in the change rate of the negative current after the start of the oxygen pumping between the crack abnormality state where cracks have occurred in the solid electrolyte layer 11 and the normal state where no cracks have occurred in the solid electrolyte layer 11. Therefore, by using this difference, it is possible to properly determine the crack abnormality of the solid electrolyte layer 11.

A configuration is provided in which as means for determining abnormalities of the sensor element 10, the clogging and crack abnormalities of the diffusion resistance layer 12 are determined during a fuel cut of the engine, whereas the crack abnormality of the solid electrolyte layer 11 is determined during the operation other than fuel cuts (during the stoichiometric-ratio operation in the present embodiment). Consequently, it is possible to suitably identify these abnormalities separately from each other.

Next, modifications in the first embodiment will be described.

(First Modification)

Figure 8:
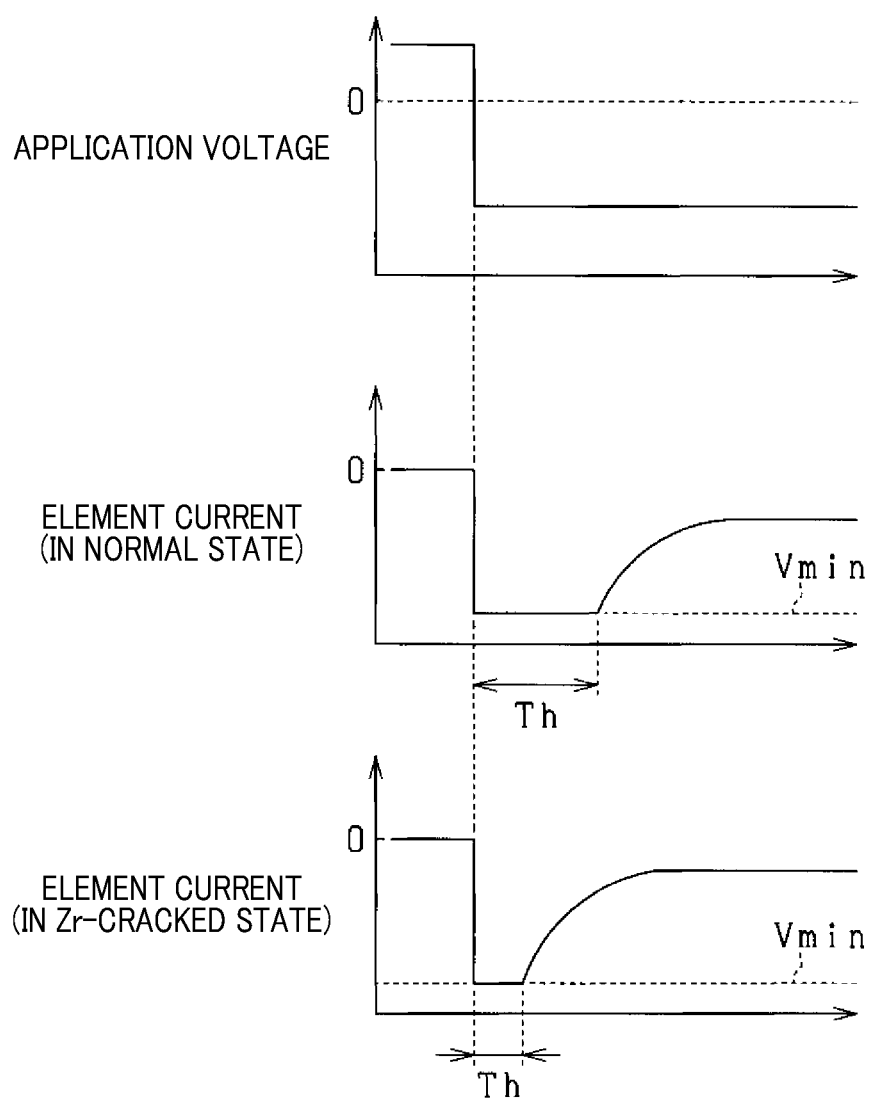
FIG. 8 is a time chart illustrating the changes with time in the applied voltage and the element current in the normal state and in the Zr-cracked state according to a first modification.

In the microcomputer 20 (detection portion of the element current), when the A/F output voltage outputted from the amplifier circuit 37 is A/D-converted, the conversion process is performed within a predetermined voltage range (e.g., 0-5V) set in advance, and values that exceed an upper limit value or a lower limit value of the voltage range are clamped to the upper limit value or the lower limit value. In this case, when the oxygen pumping is performed upon application of the negative voltage, the A/F output voltage is in the state of being clamped to the lower limit value, and the clamping time varies depending on the oxygen pumping quantity. Referring to FIG. 8, in the normal state, the clamping time Th for which the element current is clamped to the lower limit value Vmin is relatively long. In the Zr-cracked state, the clamping time Th is short in comparison with the normal state (or no clamping is considered to occur). Therefore, after the start of the oxygen pumping, the microcomputer 20 calculates the clamping time for which the sensing value of the element current (the A/F output voltage) is in the state of being clamped to a limit value (the lower limit value Vmin) of the A/D voltage range, and determines that the Zr-cracked abnormality has occurred when the clamping time is shorter than a predetermined time.

(Second Modification)

Figure 9:
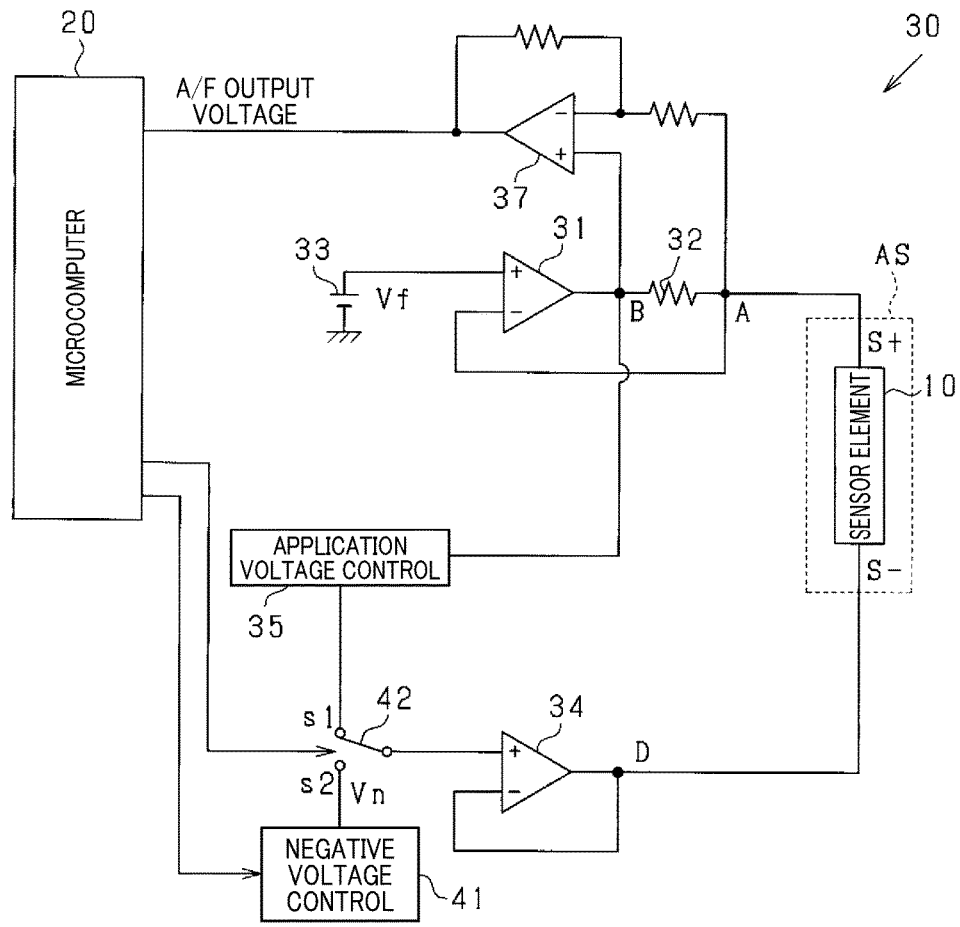
FIG. 9 is a schematic view illustrating the overall configuration of a gas sensor control apparatus according to a second modification.

In shifting the sensor application voltage VP to the negative voltage, it is possible to variably set the negative voltage. In this case, in the sensor control circuit 30, as shown in FIG. 9, a negative voltage control circuit 41 is newly provided; whether to perform the application voltage control by the application voltage control circuit 35 or to perform the application voltage control by the negative voltage control circuit 41 is switched by a switch circuit 42. When the switch circuit 42 is switched to the s1 point side, the application voltage control is performed by the application voltage control circuit 35; when the switch circuit 42 is switched to the s2 point side, the application voltage control is performed by the negative voltage control circuit 41. To the negative voltage control circuit 41 and the switch circuit 42, there are respectively inputted control commands from the microcomputer 20.

(Third Modification)

Figure 10:
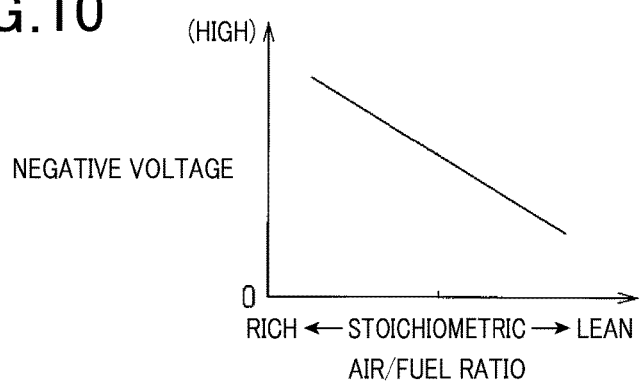
FIG. 10 is a schematic view illustrating the relationship between the air/fuel ratio and a negative voltage according to a third modification.

In the microcomputer 20, the Zr-cracked abnormality is determined in a state (but except for a fuel cut state) other than the stoichiometric-ratio operating state. The negative voltage is variably set according to the air/fuel ratio (the oxygen concentration in the exhaust gas) at each time. Specifically, at step S23 of FIG. 7, using the relationship of FIG. 10, the negative voltage is set based on the air/fuel ratio at each time. In FIG. 10, the negative voltage is set to be high on the rich side of the stoichiometric ratio and low on the lean side. Then, the negative voltage is applied between the pair of electrodes 15 and 16 to perform the oxygen pumping.

If the air/fuel ratio (the oxygen concentration in the exhaust gas) varies, the oxygen pumping quantity also varies in each of the normal state and the Zr-cracked state. In this regard, it is possible to improve the accuracy of the abnormality determination by varying the value of the negative voltage according to the air/fuel ratio.

(Fourth Modification)

It is also possible to variably set the negative voltage according to the temperature of the sensor element 10 (the element temperature). Specifically, it is possible to set the negative voltage to be high when the element temperature is lower than the activation temperature and low when the element temperature is higher than the activation temperature.

(Fifth Modification)

It is also possible to variably set the negative voltage according to the atmospheric pressure. Specifically, it is possible to set the negative voltage to be high when the atmospheric pressure is low and low when the atmospheric pressure is high.

Second Embodiment

Next, with respect to a second embodiment, the differences from the above first embodiment will be mainly described. In the first embodiment, the oxygen pumping is performed from the atmospheric air duct 18 to the exhaust gas chamber 17 by applying the negative voltage between the pair of electrodes 15 and 16 of the sensor element 10; in this state, the crack abnormality of the solid electrolyte layer 11 is determined based on the change in the negative current. In the present embodiment, the oxygen pumping is performed from the atmospheric air duct 18 to the exhaust gas chamber 17 by supplying negative current to flow between the pair of electrodes 15 and 16 of the sensor element 10; in this state, the crack abnormality of the solid electrolyte layer 11 is determined based on the sensor electromotive force.

The configuration of a sensor control circuit 30 according to the present embodiment will be described with reference to FIG. 11 (a)-(b). The configuration of the sensor control circuit 30 shown in FIG. 11 (a)-(b) differs from the configuration shown in FIG. 1 in that: a constant-current circuit is provided, as means for generating constant current, in an electrical path connected to either of the electrodes 15 and 16; and the supply of oxygen from the atmospheric air duct 18 to the exhaust gas chamber 17 is performed by the constant-current circuit. In addition, in FIG. 11 (a)-(b), the same reference signs are assigned to the same configuration as in FIG. 1; part of the same configuration (e.g., the microcomputer 20 and the like) is omitted or simplified.

In FIG. 11(a), to the positive terminal (S+ terminal) of the sensor element 10, there is connected a switch circuit 51 that is switch-operated according to a control command (switching control signal) from the microcomputer (not shown). In such a case, the switch circuit 51 is normally connected at an s1 point; in this state, a normal control of the A/F sensor AS is performed. In contrast, when the switch circuit 51 is connected at an s2 point, a constant-current circuit 52 is connected to the positive terminal (S+ terminal) of the sensor element 10. The constant-current circuit 52 is a sink-type constant-current circuit. With the constant-current circuit 52, negative current In in the direction from the electrode 15 (S−) to the electrode 16 (S+) flows in the sensor element 10.

FIG. 11(b) differs from FIG. 11(a) in that a switch circuit 53 and a constant-current circuit 54 are connected to the negative terminal (S− terminal) of the sensor element 10. The constant-current circuit 54 is a source-type constant-current circuit. With the constant-current circuit 54, negative current In in the direction from the electrode 15 (S−) to the electrode 16 (S+) flows in the sensor element 10.

Figure 12:
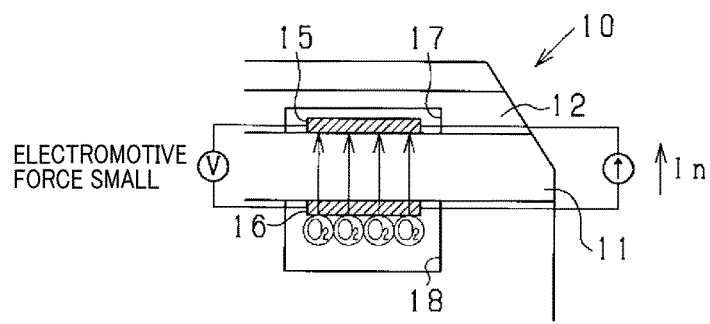
FIG. 12 is a schematic view illustrating a normal state and a Zr-cracked state of a sensor element.
Figure 13:
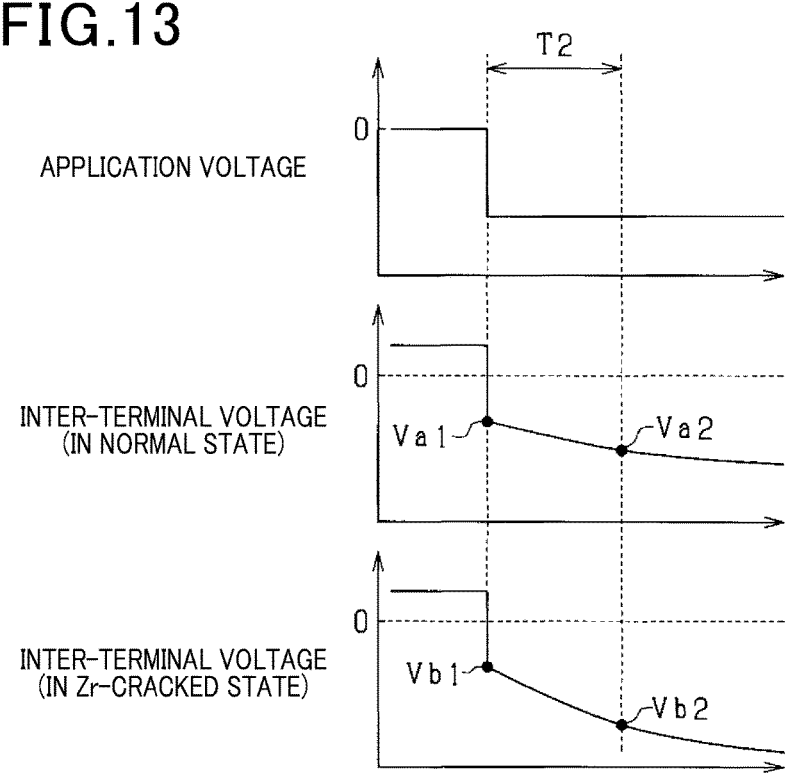
FIG. 13 is a time chart illustrating the changes with time of an element current and an inter-terminal voltage in the normal state and in the Zr-cracked state.

The principle of detection of the crack abnormality by the negative current application will be described in detail. FIG. 12 illustrates the sensor element 10 in the normal state and in the Zr-cracked state. FIG. 13 illustrates the changes with time of the element current and the inter-terminal voltage of the sensor element 10 (i.e., the voltage between the pair of electrodes 15 and 16) in the normal state and in the Zr-cracked state. In addition, here, the case is illustrated where the sensor application voltage (positive voltage) is interrupted and the element current is changed from 0 mA to a predetermined negative current in a stoichiometric ratio detection state.

First, the normal state will be described. In the normal state, the inside of the atmospheric air duct 18 is kept at the same oxygen concentration (20.9%) as the atmosphere. Moreover, in this state, when the element current is changed from 0 mA to the negative current, oxygen is pumped from the atmospheric air duct 18 side to the exhaust gas chamber 17 side. Consequently, the negative electromotive force is generated, as the inter-terminal voltage, between the pair of electrodes 15 and 16. Then, in the state of application of the negative current, the electromotive force is gradually increased to the negative side.

In this case, the electromotive force immediately after shifting the element current to the negative current is Va1; the electromotive force at a time point after the elapse of a time T2 from the electric current shifting is Va2. That is, for the period T2 of transient change, the electromotive force is changed from Va1 to Va2.

Next, the Zr-cracked state will be described. In the Zr-cracked state, the exhaust gas chamber 17 and the atmospheric air duct 18 communicate with each other via the cracks of the solid electrolyte layer 11. With the exhaust gas flowing into the atmospheric air duct 18, the oxygen concentration in the atmospheric air duct 18 becomes lower than that in the atmosphere (lower than 20.9%). Moreover, in this state, when the element current is changed from 0 mA to the negative current, oxygen is pumped from the atmospheric air duct 18 side to the exhaust gas chamber 17 side. Consequently, the negative electromotive force is generated, as the inter-terminal voltage, between the pair of electrodes 15 and 16; then the electromotive force is gradually increased to the negative side.

In this case, the electromotive force immediately after shifting the element current to the negative current is Vb1; the electromotive force at a time point after the elapse of a time T2 from the electric current shifting is Vb2. That is, for the period T2 of transient change, the electromotive force is changed from Vb1 to Vb2.

Comparing the normal state and the Zr-cracked state, the electromotive force values immediately after the shifting to the negative current are approximately equal. However, the electromotive force changes after that are different. The electromotive force change in the Zr-cracked state is more rapid than the electromotive force change in the normal state. Therefore, |Va2|<|Vb2|, and (Va2−Va1)<(Vb2−Vb1).

In short, in the Zr-cracked state, the exhaust gas flows into the atmospheric air duct 18 and thus the oxygen concentration in the atmospheric air duct 18 becomes low. Therefore, when oxygen pumping is performed from the atmospheric air duct 18 side to the exhaust gas chamber 17 side, the oxygen in the atmospheric air duct 18 is quickly reduced and thus the sensor electromotive force becomes large. In the present embodiment, based on the difference in the change rate of the sensor electromotive force, occurrence of the Zr-cracked abnormality in the sensor element 10 is determined.

Figure 14:
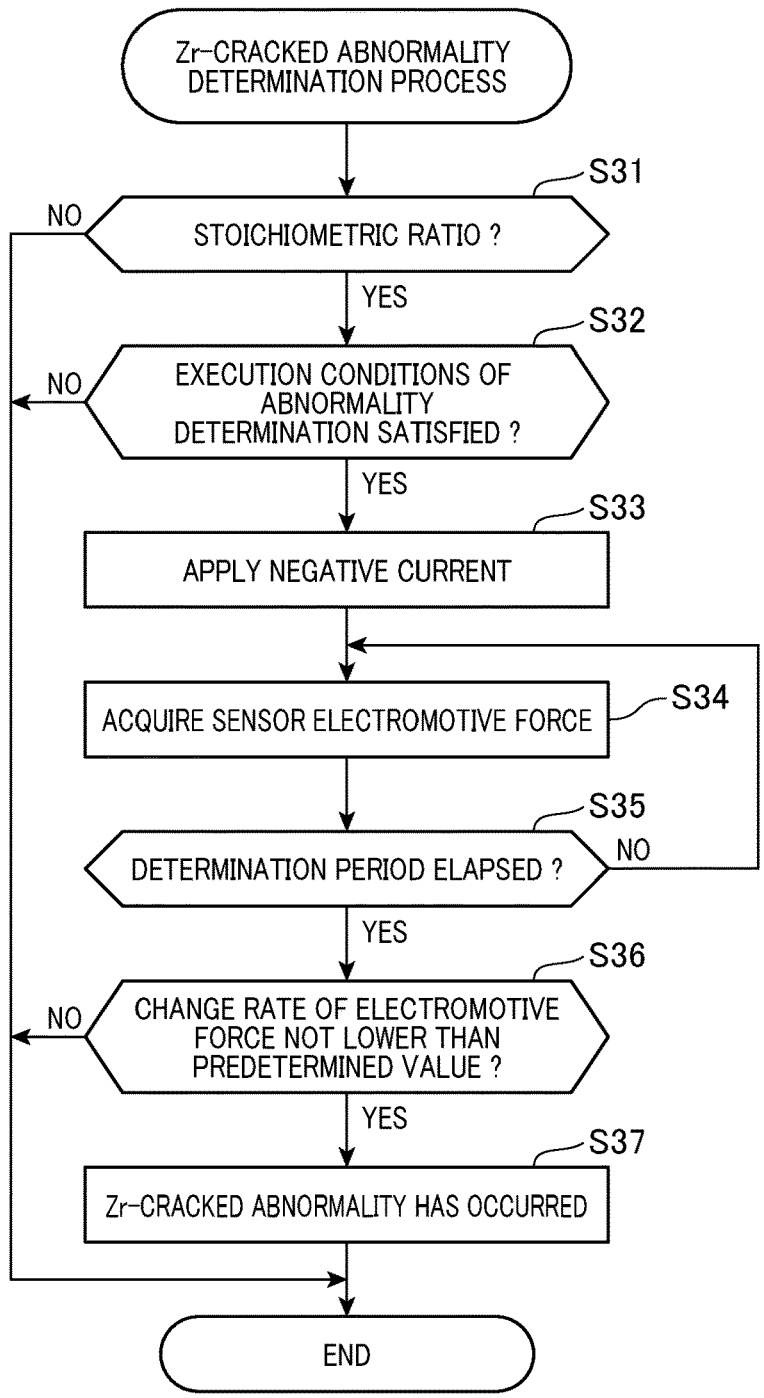
FIG. 14 is a flow chart illustrating the steps of a Zr-cracked abnormality determination process according to the second embodiment.

Next, the determination process of the crack abnormality of the solid electrolyte layer 11 (Zr-cracked abnormality) will be described. FIG. 14 is a flow chart illustrating the steps of the Zr-cracked abnormality determination process. This process is repeatedly performed by the microcomputer 20 in a predetermined cycle.

In FIG. 14, at step S31, it is determined whether or not the engine is currently in the stoichiometric-ratio operating state. At subsequent step S32, it is further determined whether execution conditions of the abnormality determination are satisfied. These steps S31 and S32 are respectively identical to the steps S21 and S22 in FIG. 7. If steps S31 and S32 are both YES, the process proceeds to step S33. On the other hand, if either of steps S31 and S32 is NO, the process directly goes to the end.

At step S33, the negative current is applied to the pair of electrodes 15 and 16 of the sensor element 10. At subsequent step S34, the value of the sensor electromotive force generated in the state of application of the negative current is acquired. The acquisition of the electromotive force value is repeatedly performed in a predetermined time cycle until the elapse of a predetermined abnormality determination period (i.e., until step S35 is determined in the affirmative).

If the predetermined abnormality determination period has elapsed and thus step S35 is determined in the affirmative, the process proceeds to step S36. At step S36, it is determined whether or not the Zr-cracked abnormality has occurred based on the change rate (corresponding to rate parameter) of the sensor electromotive force after the start of the oxygen pumping. Specifically, it is determined whether or not the change rate of the sensor electromotive force is higher than or equal to a predetermined determination threshold value K2. The change rate of the sensor electromotive force is a parameter representing how fast the electromotive force changes with the elapse of time. For example, the change rate is a time differential value (slope of change) of the electromotive force acquired at every predetermined time. Alternatively, the change rate may be the amount of the voltage change in a predetermined time after the start of the oxygen pumping. In FIG. 13, the amount of the voltage change is (Va2−Va1) or (Vb2−Vb1).

In addition, it is also possible to set a voltage threshold value for the negative electromotive force and define the change rate of the sensor electromotive force as the time required for the sensor electromotive force to reach the voltage threshold value after the start of the oxygen pumping. In this case, the higher the change rate of the sensor electromotive force, the shorter the time required for the sensor electromotive force to reach the voltage threshold value.

The determination threshold value K2 is set with reference to the change rate of the sensor electromotive force in the normal state. If the sensor element 10 is normal, step S36 is determined in the negative. In contrast, if the Zr-cracked abnormality has occurred, step S36 is determined in the affirmative.

Moreover, if step S36 is YES, the process proceeds to step S37, at which it is determined that the Zr-cracked abnormality has occurred in the sensor element 10.

In the above second embodiment, it is possible to properly determine the crack abnormality of the solid electrolyte layer 11 as in the first embodiment. In this case, there is generated the difference in the change rate of the sensor electromotive force after the start of the oxygen pumping between the crack abnormality state where cracks have occurred in the solid electrolyte layer 11 and the normal state where no cracks have occurred in the solid electrolyte layer 11. Therefore, by using this difference, it is possible to properly determine the crack abnormality of the solid electrolyte layer 11.

In addition, in the above configuration where the oxygen pumping is performed by supplying the negative current to flow between the pair of electrodes 15 and 16, it is possible to variably set the negative current. In this case, the negative current may be variably set according to the air/fuel ratio, the element temperature and the atmospheric pressure.

Third Embodiment

Figure 15:
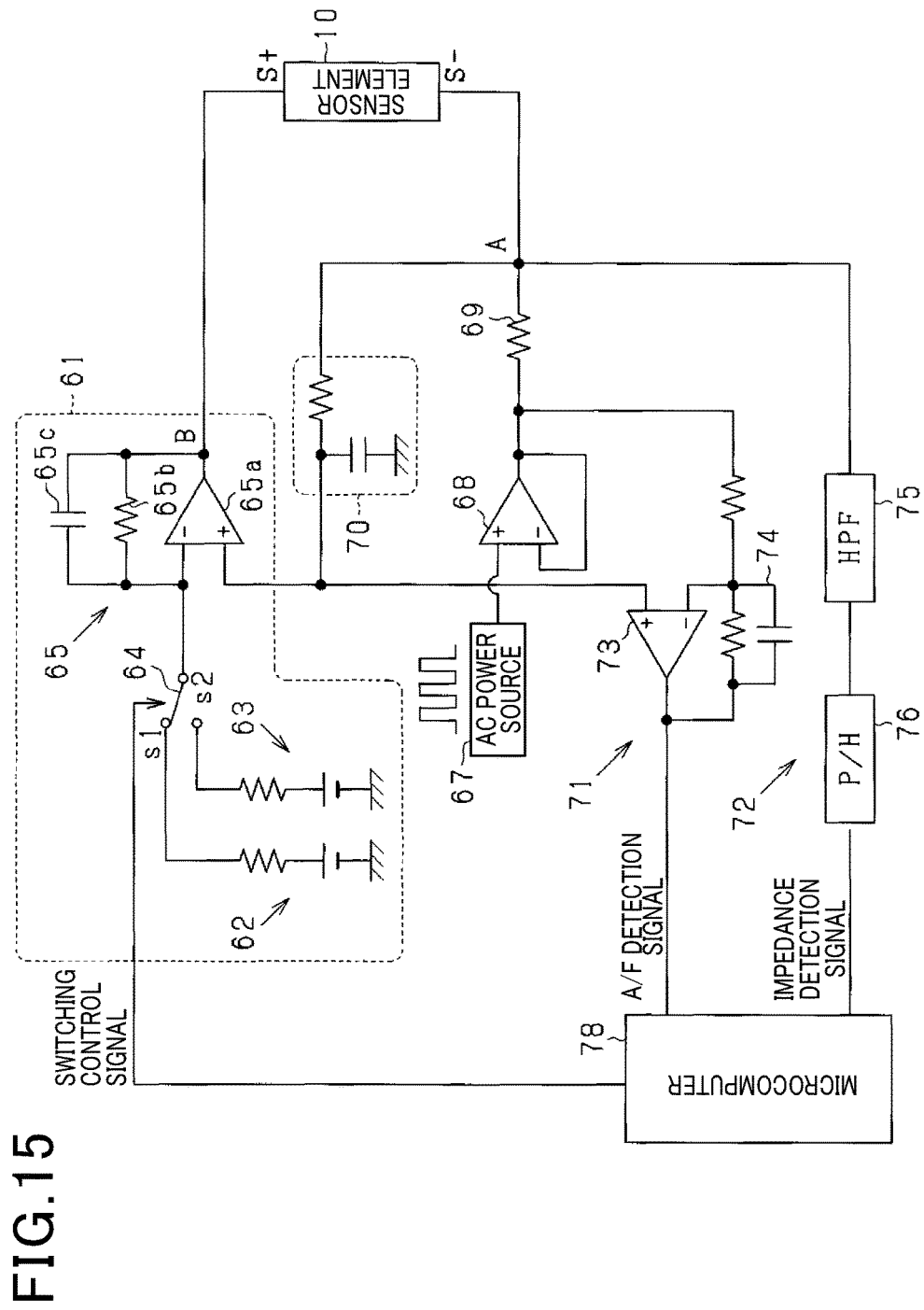
FIG. 15 is a schematic view illustrating the overall configuration of a gas sensor control apparatus according to a third embodiment.

Next, a third embodiment will be described. In this embodiment, an AC power source is used as the power source for applying voltage to the sensor element 10. FIG. 15 illustrates the overall configuration of a gas sensor control apparatus according to this embodiment.

As shown in FIG. 15, in the present embodiment, to the positive terminal (S+ terminal) of the sensor element 10, there is connected an application voltage control circuit 61. The application voltage control circuit 61 includes two power source circuits 62 and 63, a switch circuit 64 that switches the two power source circuits 62 and 63, and a non-inverting amplifier circuit 65 connected to one end of the switch circuit 64. The non-inverting amplifier circuit 65 has an operational amplifier 65a and a feedback resistor 65b connected to an inverting input terminal (− input terminal) of the operational amplifier 65a. Moreover, each of resistors included in the power source circuits 62 and 63 constitutes an input resistor of the non-inverting amplifier circuit 65. A capacitor 65c is connected parallel to the feedback resistor 65b. That is, in this configuration, there is provided an LPF for application voltage oscillation prevention integrally with the non-inverting amplifier circuit 65. The cutoff frequency fc of the LPF is, for example, 2.7 Hz.

Moreover, to the negative terminal (S− terminal) of the sensor element 10, there are serially connected an AC power source circuit 67, a buffer 68 and a current detection resistor 69. The AC power source circuit 67 is an AC voltage generation means for outputting an AC voltage of, for example, 10-20 kHz. The AC power source circuit 67 is constituted of an AC voltage generation circuit and an LPF for filter-processing the AC voltage output of the generation circuit. By the AC power source circuit 67, the AC voltage is applied to the sensor element 10. The AC power source circuit 67 corresponds to a voltage application portion for impedance detection. In the present embodiment, the AC power source circuit 67 outputs the AC voltage that has, taking 2.2V as a reference, an amplitude of 1V on both the positive and negative sides of the reference.

The current detection resistor 69 is provided in a current path between the AC power source circuit 67 and the sensor element 10. A terminal of the current detection resistor 69 on the opposite side to the sensor element 10 is set to a reference voltage (a center voltage of the AC voltage of the AC power source circuit 67). Moreover, the element current is measured at an intermediate point A between the current detection resistor 69 and the negative terminal of the sensor element 10.

Moreover, to the intermediate point A between the current detection resistor 69 and the negative terminal of the sensor element 10, there is connected an LPF 70 that is constituted of a resistor and a capacitor. Further, the LPF 70 is connected to a non-inverting input terminal (+ input terminal) of the operational amplifier 65a of the non-inverting amplifier circuit 65. In this configuration, the intermediate-point voltage between the current detection resistor 69 and the sensor element 10 (i.e., the divided voltage by the current detection resistor 69 and the sensor element 10) is inputted to the non-inverting amplifier circuit 65 of the application voltage control circuit 61 via the LPF 70. In addition, the cutoff frequency fc of the LPF 70 is, for example, 150 Hz.

In the application voltage control circuit 61, the one power source circuit 62 corresponds to a voltage application portion for the A/F detection, while the other power source circuit 63 corresponds to a voltage application portion for the negative voltage control. Moreover, the switch circuit 64 is switch-operated according to a control command (switching control signal) from the microcomputer 78. In such a case, the switch circuit 64 is normally connected at an s1 point; in this state, a normal control of the A/F sensor is performed. At this time, the power source voltage is inputted from the power source circuit 62 to the operational amplifier 65a of the non-inverting amplifier circuit 65; the output voltage of the non-inverting amplifier circuit 65 (the B-point voltage in the figure) is fixed to, for example, 2.6V. In contrast, when the switch circuit 64 is connected at an s2 point, the power source voltage is inputted from the power source circuit 63 to the operational amplifier 65a of the non-inverting amplifier circuit 65; the output voltage of the non-inverting amplifier circuit 65 (the B-point voltage in the figure) is fixed to, for example, 1.7V.

When the switch circuit 64 is connected at the s1 point and thus the output voltage of the non-inverting amplifier circuit 65 (the B-point voltage in the figure) is fixed to 2.6V, a positive voltage is applied to the sensor element 10. In contrast, when the switch circuit 64 is connected at the s2 point and thus the output voltage of the non-inverting amplifier circuit 65 (the B-point voltage in the figure) is fixed to 1.7V, a negative voltage is applied to the sensor element 10.

On the other hand, at the intermediate point A between the current detection resistor 69 and the negative terminal of the sensor element 10, there are provided two signal outputting portions so as to each separately capture the intermediate-point voltage (i.e., the divided voltage by the current detection resistor 69 and the sensor element 10). One is an A/F signal outputting portion 71 for outputting an A/F detection signal that corresponds to the element current. The other is an impedance signal outputting portion 72 for outputting an impedance detection signal. The A/F signal outputting portion 71 is constituted of a non-inverting amplifier circuit in which an operational amplifier 73 and an LPF portion 74 are integrally provided. In the A/F signal outputting portion 71, to a non-inverting input terminal (+ input terminal) of the operational amplifier 73, there is inputted the A-point voltage via the LPF 70. At this time, the varying part of the A-point voltage that alternately varies for the impedance detection is removed by the LPF 70. Moreover, the impedance signal outputting portion 72 is constituted of a HPF 75 and a peak hold circuit 76. In the peak hold circuit 76, there is integrally provided a signal amplifier portion. Both the A/F detection signal outputted from the A/F signal outputting portion 71 and the impedance detection signal outputted from the impedance signal outputting portion 72 are inputted to the microcomputer 78.

In the sensor control circuit of the above configuration, in determining the Zr-cracked abnormality, the switch circuit 64 is connected at the s2 point and thus the negative voltage, which is generated with the power source being the power source circuit 63, is applied by the application voltage control circuit 61 to the sensor element 10. Consequently, oxygen is forcibly supplied from the atmospheric air duct 18 to the exhaust gas chamber 17. Moreover, at a predetermined negative voltage control finish timing, the switch circuit 64 is switched from the s2-point connection to the s1-point connection and thus the negative voltage control is replaced by the normal control.

In the above third embodiment, it is possible to properly determine the crack abnormality of the solid electrolyte layer 11 as in the first embodiment. In addition, in the configuration using the AC power source, it is also possible to provide a constant-current circuit in the sensor control circuit and perform the oxygen pumping with a predetermined electric current (negative current) that is generated by the constant-current circuit. In this case, as in the second embodiment, there is generated a difference in the change rate of the sensor electromotive force after the start of the oxygen pumping; by using this difference, it is possible to properly determine the crack abnormality of the solid electrolyte layer 11.

(Other Modifications)

As above, the embodiments of the present invention have been described. However, the present invention is not limited to the above embodiments. For example, the above embodiments may be modified as follows.

(Sixth Modification)

Figure 16:
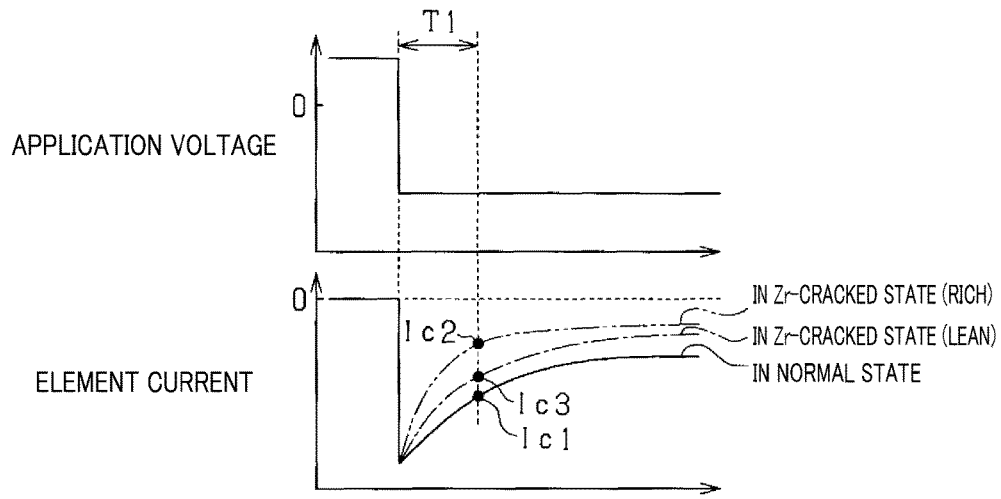
FIG. 16 is a time chart illustrating the changes with time of the applied voltage and the element current in the normal state and in the Zr-cracked state according to a sixth modification.

In the Zr-cracked abnormality determination process (FIG. 7, FIG. 14), it is possible to: acquire the air/fuel ratio (the value of the oxygen concentration in the exhaust gas) during the performing of the oxygen pumping; and variably set the determination threshold value for the crack abnormality determination of the solid electrolyte layer 11 based on the air/fuel ratio. That is, when the air/fuel ratio varies, the oxygen pumping quantity in the Zr-cracked state also varies. In this case, if the air/fuel ratio is rich, the decrease of the oxygen concentration in the atmospheric air duct 18 is relatively large; if the air/fuel ratio is lean, the decrease of the oxygen concentration in the atmospheric air duct 18 is relatively small. This relationship is shown in the time chart of FIG. 16. In FIG. 16, the change of the negative current in the normal state is indicated by a continuous line; the change of the negative current in the Zr-cracked state with the air/fuel ratio being rich is indicated by a two-dot chain line; the change of the negative current in the Zr-cracked state with the air/fuel ratio being lean is indicated by a one-dot chain line. Moreover, the values of the negative current at a time point after the elapse of a time T1 from the voltage shifting are respectively Ic1, Ic2 and Ic3 ($|Ic2|<|Ic3|<|Ic1|$).

Figure 17:
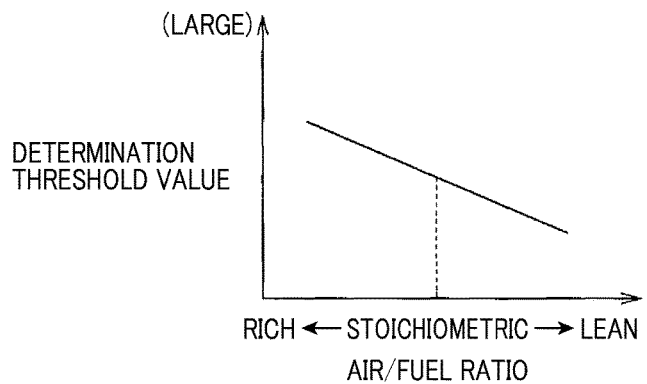
FIG. 17 is a schematic view illustrating the relationship between the air/fuel ratio and a determination threshold value according to the sixth modification.

In FIG. 16, comparing the change of the negative current in the Zr-cracked state with the air/fuel ratio being rich and the change of the negative current in the Zr-cracked state with the air/fuel ratio being lean, the former is greater in the change rate of the negative current. That is, with the air/fuel ratio being rich, it is more difficult for the negative current to flow. In this case, in detecting the Zr-cracked abnormality with the air/fuel ratio being rich, it is preferable to set the determination threshold value for the abnormality determination between Ic2-Ic3; in detecting the Zr-cracked abnormality with the air/fuel ratio being lean, it is preferable to set the determination threshold value for the abnormality determination between Ic3-Ic1. Specifically, the determination threshold value may be set using the relationship of FIG. 17. In FIG. 17, the determination threshold value is set to be large on the rich side of the stoichiometric ratio and small on the lean side.

With the above configuration, it is possible to improve the accuracy of the abnormality determination by varying the determination threshold value for the abnormality determination according to the air/fuel ratio (the oxygen concentration in the exhaust gas) at each time. Moreover, since the abnormality determination is performed not only during the stoichiometric-ratio operation, it is possible to increase the chances of performing the abnormality determination.

(Seventh Modification)

When the oxygen concentration in the atmosphere varies, the oxygen pumping quantity also varies. Therefore, it is possible to variably set the determination threshold value according to the atmospheric pressure. When the atmospheric pressure is low, as shown in FIG. 16 as the case of the air/fuel ratio being rich, the decrease of the oxygen concentration in the atmospheric air duct 18 is relatively large. By taking this fact into account, the determination threshold value may be variably set.

(Eighth Modification)

Figure 18:
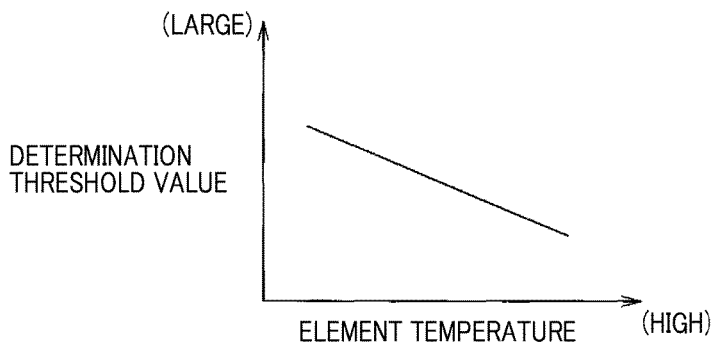
FIG. 18 is a schematic view illustrating the relationship between an element temperature and the determination threshold value according to an eighth embodiment.

In the Zr-cracked abnormality determination process (FIG. 7, FIG. 14), it is possible to: acquire the temperature of the sensor element 10 (the element impedance) during the performing of the oxygen pumping; and variably set the determination threshold value for the crack abnormality determination of the solid electrolyte layer 11 based on the element temperature. That is, when the element temperature varies, the activation state of the sensor element 10 also varies, causing the oxygen pumping quantity in the Zr-cracked state to vary. In this case, the lower the element temperature, the less the oxygen pumping quantity. Therefore, as shown in FIG. 18, if the element temperature is low, the determination threshold value is set to be large; if the element temperature is high, the determination threshold value is set to be small.

With the above configuration, it is possible to improve the accuracy of the abnormality determination by varying the determination threshold value for the abnormality determination according to the element temperature (the element impedance) at each time. Moreover, since the abnormality determination is performed not only at the element activation temperature, it is possible to increase the chances of performing the abnormality determination.

(Ninth Modification)

In the Zr-cracked abnormality determination process (FIG. 7, FIG. 14), it is possible to identify, in addition to determining the presence or absence of the crack abnormality of the solid electrolyte layer 11, the degree of the abnormality based on the negative current between the pair of electrodes 15 and 16 which is generated with the start of the oxygen pumping (step S27). Alternatively, it is possible to identify, in addition to determining the presence or absence of the crack abnormality of the solid electrolyte layer 11, the degree of the abnormality based on the sensor electromotive force that is generated with the start of the oxygen pumping (step S37).

In short, when the degree of the crack abnormality of the solid electrolyte layer 11 varies, the pace of decrease of the oxygen concentration in the atmospheric air duct 18 also varies to influence the oxygen pumping quantity in the abnormality determination. For example, the larger the cracks of the solid electrolyte layer 11, the more the oxygen concentration in the atmospheric air duct 18 decreases and thus the less the oxygen pumping quantity becomes. In this case, the degree of the abnormality is reflected in the change rate of the element current or the change rate of the sensor electromotive force; therefore, when the crack abnormality of the solid electrolyte layer 11 has occurred, it is possible to make a determination as to, for example, whether the crack abnormality can be dealt with through a correction of the sensor output value or the occurrence of the crack abnormality is identified as a failure occurrence and thus the sensor output value cannot be used.

(Tenth Modification)

Besides the A/F sensor AS, the present invention can also be applied to a so-called $O_2$ sensor whose electromotive force output changes according to the oxygen concentration in the exhaust gas.

(Eleventh Modification)

The present invention can also be embodied as sensor control apparatuses for gas sensors provided in engine intake passages or gas sensors used in engines other than gasoline engines, such as diesel engines. In addition, the gas sensors may be for uses other than motor vehicles.

DESCRIPTION OF REFERENCE SIGNS

10: sensor element; 11: solid electrolyte layer; 12: diffusion resistance layer (diffusion layer); 15: electrode (first electrode); 16: electrode (second electrode); 18: atmospheric air duct (atmospheric air chamber); 20: microcomputer (oxygen supply means, abnormality determination means); 30: sensor control circuit (gas sensor control apparatus); AS: A/F sensor.

The invention claimed is:

1. A gas sensor control apparatus for controlling a gas sensor, the gas sensor comprising a sensor element that has: a solid electrolyte layer; a first electrode arranged on one side of the solid electrolyte layer so as to be exposed to the exhaust gas of an internal combustion engine; and a second electrode arranged on the other side of the solid electrolyte layer so as to face an atmospheric air chamber, wherein the gas sensor generates a sensor output according to the oxygen concentration in the exhaust gas, the gas sensor control apparatus comprising:

a microcomputer, including storage memory and a processor, and a sensor control circuit operatively coupled to the microcomputer, wherein the microcomputer and the sensor control circuit form a configuration to at least perform:

an oxygen supply that supplies oxygen to the first electrode side from the second electrode side via the solid electrolyte layer by applying a predetermined voltage between the pair of electrodes; and an abnormality determination that calculates, after start of the oxygen supply by the oxygen supply, a rate parameter representing a change rate of electric current between the pair of electrodes which is generated with the start of the oxygen supply and determines a crack abnormality of the solid electrolyte layer based on the rate parameter, a detection that detects, within a predetermined voltage range, the electric current flowing between the pair of electrodes, and wherein the abnormality determination calculates, as the rate parameter, a clamping time for which the electric current detected by the detection is clamped to a limit value of the predetermined voltage range and determines that the crack abnormality of the solid electrolyte layer has occurred when the clamping time is shorter than a predetermined time.

2. The gas sensor control apparatus as set forth in claim 1, wherein the configuration formed the microcomputer and the sensor control circuit further performs:

an oxygen concentration acquisition that acquires a value of the oxygen concentration in the exhaust gas during the performing of the oxygen supply by the oxygen supply; and a setting that variably sets, based on the value of the oxygen concentration acquired by the oxygen concentration acquisition, the predetermined voltage or the predetermined electric current applied between the pair of electrodes in the oxygen supply.

3. The gas sensor control apparatus as set forth in claim 1, wherein the configuration formed by the microcomputer and the sensor control circuit further performs:

an oxygen concentration acquisition that requires a value of the oxygen concentration in the exhaust gas during the performing of the oxygen supply by the oxygen supply; and a setting that variably sets, based on the value of the oxygen concentration acquired by the oxygen concentration acquisition, a determination threshold value for the crack abnormality determination of the solid electrolyte layer in the abnormality determination.

4. The gas sensor control apparatus as set forth in claim 1, wherein the configuration formed by the microcomputer and the sensor control circuit further performs:

an element temperature acquisition that acquires a temperature of the sensor element during the performing of the oxygen supply by the oxygen supply; and a setting that variably sets, based on the element temperature acquired by the element temperature acquisition, a determination threshold value for the crack abnormality determination of the solid electrolyte layer in the abnormality determination.

5. The gas sensor control apparatus as set forth in claim 1, wherein the abnormality determination identifies, in addition to determining the presence or absence of the crack abnormality of the solid electrolyte layer, a degree of the abnormality based on the electric current or the electromotive force between the pair of electrodes which is generated with start of the oxygen supply by the oxygen supply.

6. The gas sensor control apparatus as set forth in claim 1, wherein the sensor element further has a diffusion layer as a path for introducing the exhaust gas to the first electrode, wherein the configuration formed by the microcomputer and the sensor control circuit further performs:

determination of an abnormality of the diffusion layer as a first determination and determination of the crack abnormality of the solid electrolyte layer as a second determination, wherein the first determination determines, when a fuel cut is performed in the internal combustion engine, the abnormality of the diffusion layer based on the sensor output of the gas sensor, and the second determination determines, when the internal combustion engine is in an operating state other than fuel cuts, the crack abnormality of the solid electrolyte layer based on the electric current or the electromotive force between the pair of electrodes which is generated by the oxygen supply.

7. A gas sensor control apparatus for controlling a gas sensor, the gas sensor comprising a sensor element that has: a solid electrolyte layer; a first electrode arranged on one side of the solid electrolyte layer so as to be exposed to the exhaust gas of an internal combustion engine; and a second electrode arranged on the other side of the solid electrolyte layer so as to face an atmospheric air chamber, wherein the gas sensor generates a sensor output according to the oxygen concentration in the exhaust gas, the gas sensor control apparatus comprising:

a microcomputer, including storage memory and a processor, and a sensor control circuit operatively coupled to the microcomputer, wherein the microcomputer and the sensor control circuit form a configuration to at least perform:

an oxygen supply that supplies oxygen to the first electrode side from the second electrode side via the solid electrolyte layer by applying a predetermined voltage between the pair of electrodes; and an abnormality determination that calculates after start of the oxygen supply by the oxygen supply, a rate parameter representing a change rate of electric current between the pair of electrodes which is generated with the start of the oxygen supply and determines a crack abnormality of the solid electrolyte layer based on the rate parameter, and wherein the abnormality determination calculates, as the rate parameter, the change rate of the electric current flowing between the pair of electrodes and determines that the crack abnormality of the solid electrolyte layer has occurred when the change rate of the electric current is higher than or equal to a predetermined value.

8. The gas sensor control apparatus as set forth in claim 7, wherein the configuration formed by the microcomputer and the sensor control circuit further performs:

an oxygen concentration acquisition that requires a value of the oxygen concentration in the exhaust gas during the performing of the oxygen supply by the oxygen supply; and a setting that variably sets, based on the value of the oxygen concentration acquired by the oxygen concentration acquisition, the predetermined voltage or the predetermined electric current applied between the pair of electrodes in the oxygen supply.

9. The gas sensor control apparatus as set forth in claim 7, wherein the configuration formed by the microcomputer and the sensor control circuit further performs:

an oxygen concentration acquisition that acquires a value of the oxygen concentration in the exhaust gas during the performing of the oxygen supply by the oxygen supply; and a setting that variably sets, based on the value of the oxygen concentration acquired by the oxygen concentration acquisition, a determination threshold value for the crack abnormality determination of the solid electrolyte layer in the abnormality determination.

10. The gas sensor control apparatus as set forth in claim 7, wherein the configuration formed by the microcomputer and the sensor control circuit further performs:

an element temperature acquisition that requires a temperature of the sensor element during the performing of the oxygen supply by the oxygen supply; and a setting that variably sets, based on the element temperature acquired by the element temperature acquisition, a determination threshold value for the crack abnormality determination of the solid electrolyte layer in the abnormality determination.

11. The gas sensor control apparatus as set forth in claim 7, wherein the abnormality determination identifies, in addition to determining the presence or absence of the crack abnormality of the solid electrolyte layer, a degree of the abnormality based on the electric current or the electromotive force between the pair of electrodes which is generated with start of the oxygen supply by the oxygen supply.

12. The gas sensor control apparatus as set forth in claim 7, wherein the sensor element further has a diffusion layer as a path for introducing the exhaust gas to the first electrode, wherein the configuration formed by the microcomputer and the sensor control circuit further performs:

determination of an abnormality of the diffusion layer as a first determination and determination of the crack abnormality of the solid electrolyte layer as a second determination, the first determination determines, when a fuel cut is performed in the internal combustion engine, the abnormality of the diffusion layer based on the sensor output of the gas sensor, and the second determination determines, when the internal combustion engine is in an operating state other than fuel cuts, the crack abnormality of the solid electrolyte layer based on the electric current or the electromotive force between the pair of electrodes which is generated by the oxygen supply.

13. A gas sensor control apparatus for controlling a gas sensor, the gas sensor comprising a sensor element that has: a solid electrolyte layer; a first electrode arranged on one side of the solid electrolyte layer so as to be exposed to the exhaust gas of an internal combustion engine; and a second electrode arranged on the other side of the solid electrolyte layer so as to face an atmospheric air chamber, wherein the gas sensor generates a sensor output according to the oxygen concentration in the exhaust gas, the gas sensor control apparatus comprising:

a microcomputer, including storage memory and a processor, and a sensor control circuit operatively coupled to the microcomputer, wherein the microcomputer and the sensor control circuit form a configuration to at least perform:

an oxygen supply that supplies oxygen to the first electrode side from the second electrode side via the solid electrolyte layer by applying a predetermined electric current between the pair of electrodes; and an abnormality determination that calculates, after start of the oxygen supply by the oxygen supply, a rate parameter representing a change rate of electromotive force between the pair of electrodes which is generated with the start of the oxygen supply and determines a crack abnormality of the solid electrolyte layer based on the rate parameter, and wherein the abnormality determination calculates, as the rate parameter, the change rate of the electromotive force generated between the pair of electrodes and determines that the crack abnormality of the solid electrolyte layer has occurred when the change rate of the electromotive force is higher than or equal to a predetermined value.

14. The gas sensor control apparatus as set forth in claim 13, wherein the configuration formed by the microcomputer and the sensor control circuit further performs:
an oxygen concentration acquisition that acquires a value of the oxygen concentration in the exhaust gas during the performing of the oxygen supply by the oxygen supply; and
a setting that variably sets, based on the value of the oxygen concentration acquired by the oxygen concentration acquisition, the predetermined voltage or the predetermined electric current applied between the pair of electrodes in the oxygen supply.

15. The gas sensor control apparatus as set forth in claim 13, wherein the configuration formed by the microcomputer and the sensor control circuit further performs:
an oxygen concentration acquisition that acquires a value of the oxygen concentration in the exhaust gas during the performing of the oxygen supply by the oxygen supply; and
a setting that variably sets, based on the value of the oxygen concentration acquired by the oxygen concentration acquisition, a determination threshold value for the crack abnormality determination of the solid electrolyte layer in the abnormality determination.

16. The gas sensor control apparatus as set forth in claim 13, wherein the configuration formed by the microcomputer and the sensor control circuit further performs:
an element temperature acquisition that requires temperature of the sensor element during the performing of the oxygen supply by the oxygen supply; and
a setting that variably sets, based on the element temperature acquired by the element temperature acquisition, a determination threshold value for the crack abnormality determination of the solid electrolyte layer in the abnormality determination.

17. The gas sensor control apparatus as set forth in claim 13, wherein the abnormality determination identifies, in addition to determining the presence or absence of the crack abnormality of the solid electrolyte layer, a degree of the abnormality based on the electric current or the electromotive force between the pair of electrodes which is generated with start of the oxygen supply by the oxygen supply.

18. The gas sensor control apparatus as set forth in claim 13, wherein the sensor element further has a diffusion layer as a path for introducing the exhaust gas to the first electrode,
wherein the configuration formed by the microcomputer and the sensor control circuit further performs:
determination of an abnormality of the diffusion layer as a first determination and determination of the crack abnormality of the solid electrolyte layer as a second determination,
the first determination determines, when a fuel cut is performed in the internal combustion engine, the abnormality of the diffusion layer based on the sensor output of the gas sensor, and
the second determination determines, when the internal combustion engine is in an operating state other than fuel cuts, the crack abnormality of the solid electrolyte layer based on the electric current or the electromotive force between the pair of electrodes which is generated by the oxygen supply.

* * * * *